United States Patent [19]

Oi et al.

[11] Patent Number: 5,788,914
[45] Date of Patent: Aug. 4, 1998

[54] NEAR INFRARED RAY ABSORBING COMPOUND HAVING HIGH DURABILITY AND ITS USE

[75] Inventors: Ryu Oi; Kazuhiro Seino, both of Yokohama; Yuko Mochizuki, Nagoya; Keisuke Takuma, Yokohama, all of Japan

[73] Assignees: Mitsui Chemicals, Inc., Tokyo; Yamamoto Chemicals, Inc., Yao, both of Japan

[21] Appl. No.: 721,022

[22] Filed: Sep. 26, 1996

[51] Int. Cl.$^6$ .............................. F21V 9/04; C09B 47/04; C07D 487/22
[52] U.S. Cl. .................. 252/587; 540/125; 540/139; 540/140
[58] Field of Search ................ 252/587; 540/125, 540/139, 140

[56] References Cited

U.S. PATENT DOCUMENTS 4,824,947  4/1989  Stark ........................ 540/125

FOREIGN PATENT DOCUMENTS

| | | |
|---|---|---|
| 282181 | 9/1988 | European Pat. Off. . |
| 0484018 | 5/1992 | European Pat. Off. . |
| 0519395 | 12/1992 | European Pat. Off. . |
| 1172961 | 2/1959 | France . |
| 63-270765 | 11/1988 | Japan . |
| 63-308073 | 12/1988 | Japan . |
| 75916 | 12/1992 | Japan . |
| 1029433 | 5/1966 | United Kingdom . |

OTHER PUBLICATIONS

Patent Abstracts of Japan, vol. 013, No. 084, (c–572), Feb. 1989 & JP–63–270765 A, (Mitsui Toastsu Chemicals, Inc.), Nov. 1988 *abstract*.

*Primary Examiner*—Philip Tucker
*Attorney, Agent, or Firm*—Burns, Doane, Swecker & Mathis, L.L.P.

[57] ABSTRACT

A near infrared ray absorbing compound having an improved solubility and light resistance can be obtained by amidating and/or imidating the amino groups on substituents of a phthalocyanine. According to its preparation process, the desired near infrared ray absorbing compound can be easily prepared by reacting the phthalocyanine having an elimination group such as a halogen atom with a 2-aminothiophenol derivative, and then amidating and/or imidating a part or all of the remaining primary or secondary amino groups. Moreover, substituents on the benzene rings of the phthalocyanine can be coordinated with metals, whereby an absorption wavelength can be broadened and the near infrared rays in a long wave range can be absorbed. The near infrared ray absorbing compound of the present invention is useful as a heat ray absorbing material.

12 Claims, 2 Drawing Sheets

NEAR INFRARED RAY ABSORBING COMPOUND HAVING HIGH DURABILITY AND ITS USE

BACKGROUND OF THE INVENTION

1. Field of the Invention

The present invention relates to a near infrared ray absorbing compound which is excellent in durability (especially stability to light) and solubility and of which work and treatment can easily be done, and a simple process for preparing the near infrared ray absorbing compound. Furthermore, the present invention relates to a near infrared ray absorbing resin composition which contains this near infrared ray absorbing compound, and a heat ray absorbing material containing the compound.

2. Description of the Related Art

A near infrared ray absorbing compound can be utilized in the recording layer of an optical storage medium such as an optical disk, and when an ink is made from this compound, the ink can be utilized as a near infrared ray absorbing ink which can be read by a near infrared ray detector. Furthermore, the near infrared ray absorbing compound can be combined with a binder resin to prepare a coating material, and this coating material can be then applied onto a plastic plate or a glass plate, or can be kneaded with a resin to prepare a near infrared ray absorbing material.

When the near infrared ray absorbing material is utilized as a window material of a building, a car, a train, a ship, an airplane or the like, heat rays from the outside can be intercepted, whereby the rise of its inside temperature can be restrained. Since the near infrared ray absorbing material can intercept a specific wave range, it can be utilized as a film for agriculture using a selected light quantity to control the growth of plant, as a light receiving semiconductor element for intercepting infrared rays, or as spectacles which protect human eyes from light including harmful infrared rays.

Above all, the near infrared ray absorbing material which aims at the interception of the heat rays can contribute to saving energy, and therefore much attention is especially paid to this kind of material.

As the window material suitable for the heat ray interception, a heat ray reflecting filter is known which can be obtained by alternately laminating a metallic oxide such as indium oxide or tin oxide and a metal such as gold or silver on a PET film or a glass plate, but such a heat ray reflecting filter has been manufactured in accordance with a complicated manufacturing process, so that product cost is high, and what is worse, it has caused jamming of electronic signals. In contrast to inorganic type heat ray reflecting filters, a near infrared ray absorbing filter in which a near infrared ray absorbing dyestuff is used can be simply manufactured and has no problem of the jamming, and for these reasons, its application field is wide and its demand in a market is also large. However, from the viewpoints of the cost and the durability (especially stability to light) of the dyestuff, the employment of this near infrared ray absorbing filter has not been spread so far.

As an organic dyestuff which can absorb the near infrared rays, a cyanine dye is heretofore well known. However, the cyanine dye is extremely poor in light-resistance, so that many restrictions are unavoidably put on the employment of this dye. Furthermore, an aminium salt type compound or a dithiol metallic complex compound is insufficient in points of heat resistance and light resistance. In addition, an anthraquinone compound is also insufficient in point of light resistance, though its heat resistance is good.

As near infrared ray absorbing dyestuffs having a high durability, phthalocyanines are known, but the $\lambda_{max}$ of the phthalocyanines are as short as at most 800 nm, and for the purpose of the heat ray absorption, they are insufficient.

In examples described in Japanese Patent Publication No. 75916/1992 (U.S. Pat. No. 4,606,859), a chlorinated copper phthalocyanine is reacted with 2-aminothiophenol to obtain a dyestuff having a $\lambda_{max}$ of 909 nm, but this $\lambda_{max}$ value is measured in pyridine, and neither data of coating on a glass plate nor data of extinction coefficients are present. That is to say, the solubility of this dyestuff compound in an organic solvent suitable for a coating method or a resin is low, and therefore, if the compound is dissolved in the resin in order to manufacture a near infrared ray absorbing filter, a fogging phenomenon occurs, so that transparent resin plates and films cannot be obtained.

Furthermore, in Japanese Patent Application Laid-open No. 308073/1988 (U.S. Pat. No. 4,824,947), it has been disclosed that a phthalocyanine is reacted in the presence of 2-aminothiophenol and 4-methylthiophenol for the purpose of increasing-the solubility of the phthalocyanine, and in Japanese Patent Application Laid-open No. 270765/1988, it has been disclosed that a perchlorocopper phthalocyanine (trade name Phthalocyanine Green) is reacted with 2-aminothiophenol, and a nitrogen atom is then alkylated with an alkyl bromide to improve the solubility. In both the cases, the elongation of the absorption wavelength is attempted by introducing an amino group, but the amino group itself easily suffers light oxidation to generate radicals and the like, so that the phthalocyanine ring decomposes. Accordingly, in the products obtained by these disclosed methods, the durability to light is poor.

In addition, the phthalocyanine compound has been obtained through many manufacturing steps and it is also expensive, and for these reasons, the industrial employment of the phthalocyanine compound has been improper.

SUMMARY OF THE INVENTION

An object of the present invention is to inexpensively and simply provide a highly soluble phthalocyanine-based near infrared ray absorbing compound having a high light resistance, particularly a near infrared ray absorbing dyestuff which is effective as a heat ray absorbing material.

Another object of the present invention is to provide a near infrared ray absorbing resin composition containing this near infrared ray absorbing dyestuff.

Still another object of the present invention is to provide a heat ray absorbing material containing the near infrared ray absorbing dyestuff.

The present inventors have intensively investigated in order to achieve the above-mentioned objects, and as a result, it has been found that when a part or all of the amino groups on substituents of a phthalocyanine are amidated and/or imidated, a near infrared ray absorbing dyestuff having an improved solubility and light resistance can be obtained. It has also been found that the desired near infrared ray absorbing compound can be prepared by reacting a phthalocyanine having one or more elimination groups such as a halogen atom with a 2-aminothiophenol derivative, and then amidating and/or imidating a part or all of the remaining primary or secondary amino groups. In consequence, the present invention has been completed. Moreover, it has also been found that when substituents on the benzene rings of the phthalocyanine are coordinated with metals, an absorption wavelength can be broadened, whereby the near infrared rays in a long wave range can be absorbed.

That is to say, the present invention is directed to a novel near infrared ray absorbing compound represented by formula (1):

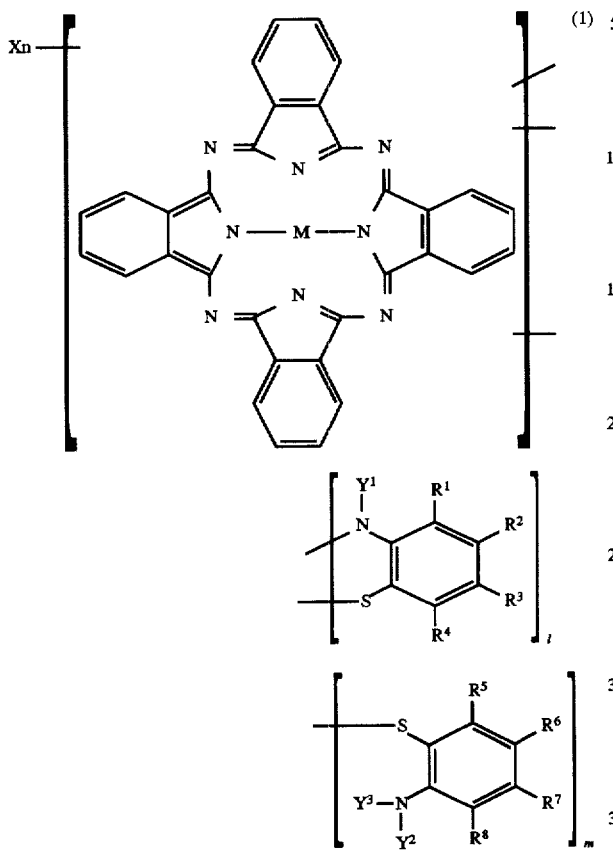

wherein each X is independently a hydrogen atom, halogen atom, hydroxyl group, alkoxy group having 1 to 20 carbon atoms, aryloxy group having 6 to 20 carbon atoms, alkylthio group having 1 to 20 carbon atoms, arylthio group having 6 to 20 carbon atoms, alkylamino group having 1 to 20 carbon atoms, arylamino group having 6 to 20 carbon atoms or alkylarylamino group having 7 to 20 carbon atoms, and the two adjacent xs may form a five-membered ring or a six-membered ring via two heteroatoms; each of $R^1$ to $R^8$ is independently a hydrogen atom, alkyl group having 1 to 20 carbon atoms, aryl group having 6 to 20 carbon atoms, alkoxy group having 1 to 20 carbon atoms or aryloxy group having 6 to 20 carbon atoms; each of $Y^1$ to $Y^3$ is independently a hydrogen atom, alkyl group having 1 to 20 carbon atoms, aryl group having 6 to 20 carbon atoms, alkylsulfonyl group having 1 to 20 carbon atoms, arylsulfonyl group having 6 to 20 carbon atoms, alkylcarbonyl group having 2 to 20 carbon atoms or arylcarbonyl group having 7 to 20 carbon atoms, and $Y^2$ and $Y^3$ on one nitrogen atom may form a cyclic imide, with the proviso that at least one of $Y^1$ to $Y^3$ is an alkylsulfonyl group having 1 to 20 carbon atoms, arylsulfonyl group having 6 to 20 carbon atoms, alkylcarbonyl group having 2 to 20 carbon atoms or arylcarbonyl group having 7 to 20 carbon atoms, or at least one pair of $Y^2$ and $Y^3$ on one independent nitrogen atom forms a cyclic imide; n is an integer of 0 to 14; l is an integer of 1 to 8; m is an integer of 0 to 14, subject to n+2l+m=16; and M is a divalent metallic atom, or a trivalent or a tetravalent substituted metal or oxymetal.

Furthermore, the present invention is directed to a process for preparing the above-mentioned near infrared ray absorbing compound having a high durability which comprises the steps of reacting a phthalocyanine represented by formula (2):

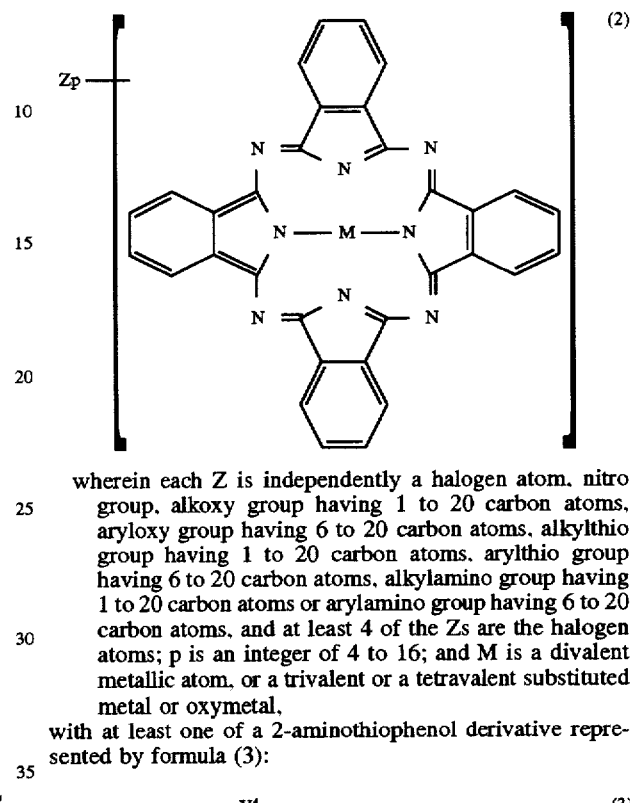

wherein each Z is independently a halogen atom, nitro group, alkoxy group having 1 to 20 carbon atoms, aryloxy group having 6 to 20 carbon atoms, alkylthio group having 1 to 20 carbon atoms, arylthio group having 6 to 20 carbon atoms, alkylamino group having 1 to 20 carbon atoms or arylamino group having 6 to 20 carbon atoms, and at least 4 of the Zs are the halogen atoms; p is an integer of 4 to 16; and M is a divalent metallic atom, or a trivalent or a tetravalent substituted metal or oxymetal, with at least one of a 2-aminothiophenol derivative represented by formula (3):

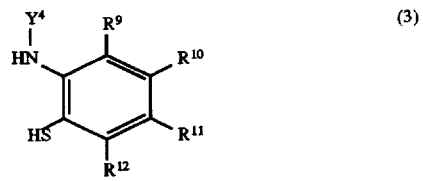

wherein $Y^4$ is a hydrogen atom, alkyl group having 1 to 20 carbon atoms or aryl group having 6 to 20 carbon atoms; and each of $R^9$ to $R^{12}$ is a hydrogen atom, alkyl group having 1 to 20 carbon atoms, aryl group having 6 to 20 carbon atoms, alkoxy group having 1 to 20 carbon atoms or aryloxy group having 6 to 20 carbon atoms, and its analogs, and then carrying out sulfonamidation and/or amidation and/or imidation.

In addition, the present invention is directed to a near infrared ray absorbing compound in which substituents on benzene rings of the phthalocyanine are coordinated with metals, the near infrared ray absorbing compound being obtainable by reacting the above-mentioned near infrared ray absorbing compound having the high durability with a metallic salt. Moreover, the present invention is directed to uses of these near infrared ray absorbing compounds.

According to the present invention, the highly soluble type phthalocyanine-based near infrared ray absorbing compound having the high durability can be provided by a simple preparation process, and this phthalocyanine-based near infrared ray absorbing compound is practically extremely valuable as a heat ray absorbing material such as a heat ray absorbing (near infrared ray absorbing) coating material and a heat ray absorbing filter.

DETAILED DESCRIPTION OF THE PREFERRED EMBODIMENTS

Figure 1:
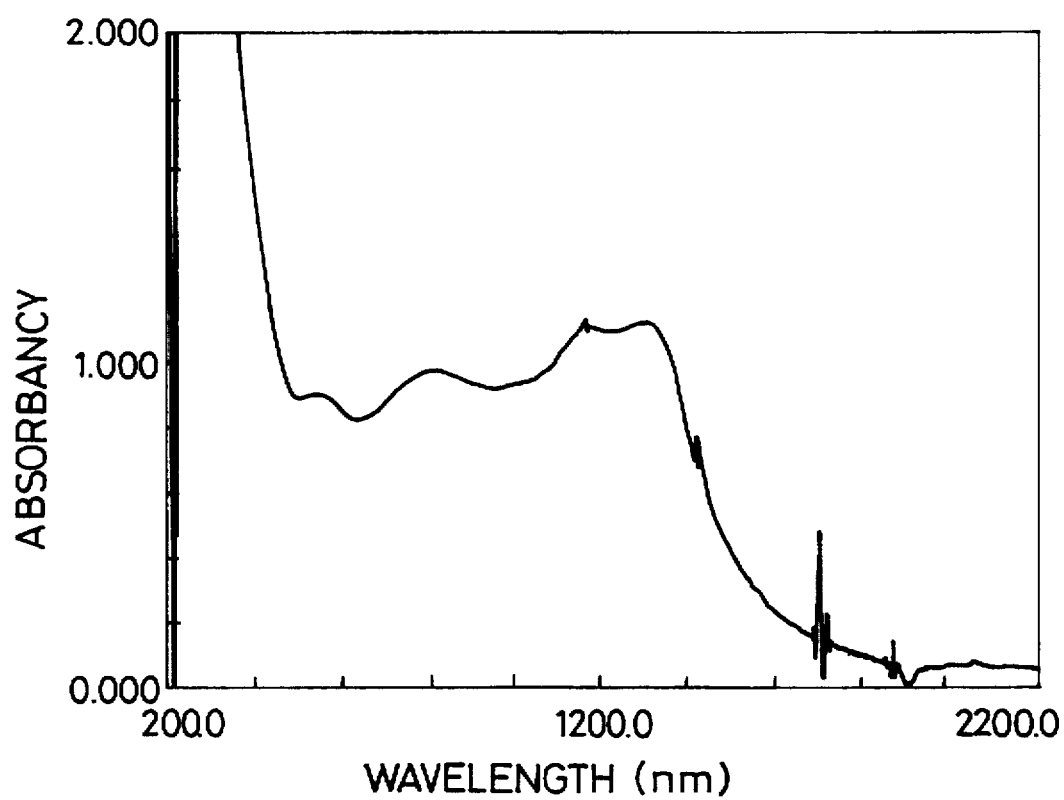
FIG. 1 is a graph showing the absorbancy spectrum of a compound obtained in Example 15.

In a near infrared ray absorbing dyestuff represented by formula (1) of the present invention, examples of a halogen atom represented by X include fluorine, chlorine, bromine and iodine. No particular restriction is put on an alkoxy group having 1 to 20 carbon atoms, and examples of the alkoxy group include a methoxy group, ethoxy group, n-propoxy group, iso-propoxy group, n-butoxy group, iso-butoxy group, sec-butoxy group, n-pentoxy group, iso-pentoxy group, n-hexyloxy group, cyclohexyloxy group, n-heptyloxy group, n-octyloxy group, 2-ethylhexyloxy group, n-nonyloxy group, methoxyethoxy group, ethoxyethoxy group, ethoxyethoxyethoxy group, hydroxyethoxyethoxy group, diethylaminoethoxy group, aminoethoxy group, n-butylaminoethoxy group, benzylaminoethoxy group, methylcarbonylaminoethoxy group, phenylcarbonylaminoethoxy group and benzyloxy group.

No particular restriction is put on an aryloxy group having 6 to 20 carbon atoms, and examples of the aryloxy group include a phenoxy group, 2-methylphenoxy group, 3-methylphenoxy group, 4-methylphenoxy group and naphthoxy group.

No particular restriction is put on an alkylthio group having 1 to 20 carbon atoms, and examples of the alkylthio group include a methylthio group, ethylthio group, n-propylthio group, iso-propylthio group, n-butylthio group, iso-butylthio group, sec-butylthio group, t-butylthio group, n-pentylthio group, iso-pentylthio group, neo-pentylthio group, 1,2-dimethylpropylthio group, n-hexylthio group, cyclohexylthio group, n-heptylthio group, 2-ethylhexylthio group, n-octylthio group, n-nonylthio group, methoxyethylthio group, ethoxyethylthio group, propoxyethylthio group, butoxyethylthio group, aminoethylthio group, n-butylaminoethylthio group, benzylaminoethylthio group, methylcarbonylaminoethylthio group, phenylcarbonylaminoethylthio group, methylsulfonylaminoethylthio group, pheylsulfonylaminoethylthio group, dimethylaminoethylthio group and diethylaminoethylthio group.

No particular restriction is put on an arylthio group having 6 to 20 carbon atoms, and examples of the arylthio group include a phenylthio group, naphthylthio group, 4-methylphenylthio group, 4-ethylphenylthio group, 4-propylphenylthio group, 4-t-butylphenylthio group, 4-methoxyphenylthio group, 4-ethoxyphenylthio group, 4-aminophenylthio group, 4-alkylaminophenylthio group, 4-dialkylaminophenylthio group, 4-phenylaminophenylthio group, 4-diphenylaminophenylthio group, 4-hydroxyphenylthio group, 4-chlorophenylthio group, 4-bromophenylthio group, 2-methylphenylthio group, 2-ethylphenylthio group, 2-propylphenylthio group, 2-t-butylphenylthio group, 2-methoxyphenylthio group, 2-ethoxyphenylthio group, 2-aminophenylthio group, 2-alkylaminophenylthio group, 2-dialkylaminophenylthio group, 2-phenylaminophenylthio group, 2-diphenylaminophenylthio group, 2-hydroxyphenylthio group, 4-aminophenylthio group, 4-dimethylaminophenylthio group, 4-methylaminophenylthio group, 4-methylcarbonylaminophenylthio group, 4-phenylcarbonylaminophenylthio group, 4-methylsulfonylaminophenylthio group and 4-phenylsulfonylaminophenylthio group.

No particular restriction is put on an alkylamino group having 1 to 20 carbon atoms, and examples of the alkylamino group include a methylamino group, ethylamino group, n-propylamino group, iso-propylamino group, butylamino group, pentylamino group, dipentylamino group, hexylamino group, heptylamino group, octylamino group, nonylamino group and benzylamino group.

No particular restriction is put on an arylamino group having 6 to 20 carbon atoms, and examples of the arylamino group include a phenylamino group, 4-methylphenylamino group, 4-methoxyphenylamino group, hydroxyphenylamino group and naphthylamino group.

No particular restriction is put on an alkylarylamino group having 7 to 20 carbon atoms, and examples of the alkylarylamino group include a phenylmethylamino group, phenylethylamino group and phenylpropylamino group.

Moreover, two adjacent Xs may form a five- or six-membered ring via two hetero-atoms, and examples of such five- and six-membered ring include substituents represented by the following formulae:

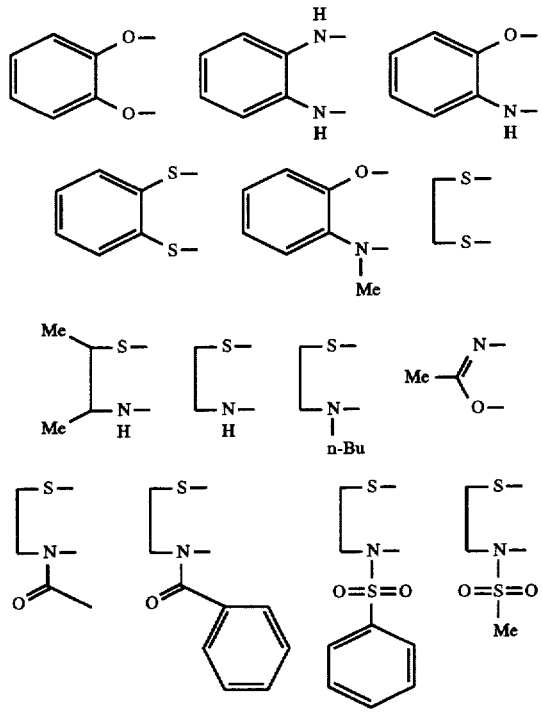

Examples of an alkyl group having 1 to 20 carbon atoms represented by $R^1$ to $R^8$ in formula (1) include a methyl group, ethyl group, n-propyl group, iso-propyl group, n-butyl group, iso-butyl group, sec-butyl group, n-pentyl group, iso-pentyl group, 1,2-dimethylpropyl group, n-hexyl group and benzyl group.

Examples of an aryl group having 6 to 20 carbon atoms include a phenyl group, 2-mercaptophenyl group, 3-mercaptophenyl group, 4-mercaptophenyl group, 2-methylphenyl group, 3-methylphenyl group, 4-methylphenyl group and naphthyl group.

Examples of an alkoxy group having 1 to 20-carbon atoms include a methoxy group, ethoxy group, n-propoxy group, iso-propoxy group, n-butoxy group, iso-butoxy group, sec-butoxy group, n-pentoxy group, iso-pentoxy group and benzy-loxy group.

Examples of an aryloxy group having 6 to 20 carbon atoms include a phenoxy group, 2-methylphenoxy group, 3-methylphenoxy group, 4-methylphenoxy group and naphthoxy group.

Examples of an alkyl group having 1 to 20 carbon atoms represented by $Y^1$ to $Y^3$ in formula (1) include a methyl group, ethyl group, n-propyl group, iso-propyl group, n-butyl group, iso-butyl group, sec-butyl group, n-pentyl group, iso-pentyl group, 1,2-dimethylpropyl group, n-hexyl group, 1,3-dimethylbutyl group, 1,2-dimethylbutyl group, n-heptyl group, 1,4-dimethylpentyl group, 1-ethyl-3-methylbutyl group, n-octyl group, 2-ethylhexyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-eicosyl group, benzyl group, sec-phenylethyl group, 2-methylbenzyl group, 3-methylbenzyl group, 4-methylbenzyl group, 2-phenylethyl group, 3-dimethylaminopropyl group, 2-dimethylaminoethyl group, 2-diisopropylaminoethyl group, 2-diethylaminoethyl group, 2,2,2-trifluoro-1-(trifluoromethyl)ethyl group, 2-(1-piperidinyl)ethyl group, 3-(1-piperidinyl)propyl group, 3-(4-morpholinyl)propyl group, 3-(4-morpholinyl)ethyl-group, 2-(1-pyrolidinyl)ethyl group, 2-pyridylmethyl group and furfuryl group.

Examples of an aryl group having 6 to 20 carbon atoms include a phenyl group, 2-mercaptophenyl group, 3-mercaptophenyl group, 4-mercaptophenyl group, 2-methylphenyl group, 3-methylphenyl group, 4-methylphenyl group and naphthyl group.

Examples of an alkylcarbonyl group having 2 to 20 carbon atoms include an acetyl group (methylcarbonyl group), propionyl group, butyryl group, iso-butyryl group, valeryl group, iso-valeryl group, trimethylacetyl group, hexanoyl group, t-butylacetyl group, heptanoyl group, octanoyl group, 2-ethylhexanoyl group, nonanoyl group, decanoyl group, undecanoyl group, lauroyl group, tridecanoyl group, tetradecanoyl group, pentadecanoyl group, hexadecanoyl group, heptadecanoyl group, octadecanoyl group, oleoyl group, cyclopentanecarbonyl group, cyclohexanecarbonyl group, 6-chlorohexanoyl group, 6-bromohexanoyl group, trifluoroacetyl group, pentafluoropropionyl group, perfluorooctanoyl group, 2,2,4,4,5,5,7,7,7-nonafluoro-3,6-dioxaheptanoyl group, methoxyacetyl group and 3,6-dioxaheptanoyl group.

Examples of an arylcarbonyl group having 7 to 20 carbon atoms include a benzoyl group, o-chlorobenzoyl group, m-chlorobenzoyl group, p-chlorobenzoyl group, o-fluorobenzoyl group, m-fluorobenzoyl group, p-fluorobenzoyl group, o-acetylbenzoyl group, m-acetylbenzoyl group, p-acetylbenzoyl group, o-methoxybenzoyl group, m-methoxybenzoyl group, p-methoxybenzoyl group, o-methylbenzoyl group, m-methylbenzoyl group, p-methylbenzoyl group, pentafluorobenzoyl group and 4-(trifluoromethyl)benzoyl group.

Examples of the alkylsulfonyl group having 1 to 20 carbon atoms include a methylsulfonyl group, ethylsulfonyl group and trifluoromethylsulfonyl group.

Examples of an arylsulfonyl group having 6 to 20 carbon atoms include a phenylsulfonyl group and 4-methylphenylsulfonyl group.

Examples of a cyclic imide group which can be formed by the use of $Y^2$ and $Y^3$ on one nitrogen atom include succinimide, maleimide and phthalimide.

Examples of a divalent metal represented by M in formula (1) include Cu(II), Zn(II), Fe(II), Co(II), Ni(II), Ru(II), Rh(II), Pd(II), Pt(II), Mn(II), Mg(II), Ti(II), Be(II), Ca(II), Ba(II), Cd(II), Hg(II), Pb(II) and Sn(II).

Examples of a mono-substituted trivalent metal include Al—Cl, Al—Br, Al—F, Al—I, Ga—Cl, Ga—F, Ga—I, Ga—Br, In—Cl, In—Br, In—I, In—F, Tl—Cl, Tl—Br, Tl—I, Tl—F, Al—$C_6H_5$, Al—$C_6H_4(CH_3)$, In—$C_6H_5$, In—$C_6H_4(CH_3)$, Mn(OH), Mn($OC_6H_5$), Mn[$OSi(CH_3)_3$], Fe—Cl and Ru—Cl.

Examples of a di-substituted tetravalent metal include $CrCl_2$, $SiCl_2$, $SiBr_2$, $SiF_2$, $SiI_2$, $ZrCl_2$, $GeCl_2$, $GeBr_2$, $GeI_2$, $GeF_2$, $SnCl_2$, $SnBr_2$, $SnF_2$, $TiCl_2$, $TiBr_2$, $TiF_2$, $Si(OH)_2$, $Ge(OH)_2$, $Zr(OH)_2$, $Mn(OH)_2$, $Sn(OH)_2$, $TiR_2$, $CrR_2$, $SiR_2$, $SnR_2$, $GeR_2$ (wherein R is an alkyl group, phenyl group, naphthyl group or its derivative), $Si(OR')_2$, $Sn(OR')_2$, $Ge(OR')_2$, $Ti(OR')_2$, $Cr(OR')_2$ (wherein R' is an alkyl group, phenyl group, naphthyl group, trialkylsilyl group, dialkylalkoxysilyl group or its derivative), $Sn(SR'')_2$ and $Ge(SR'')_2$ (R'' is an alkyl group, phenyl group, naphthyl group or its derivative).

Examples of an oxymetal include VO, MnO and TiO.

In the preferable compound represented by formula (1), each of Xs is independently a hydrogen atom or a halogen atom, and each of $R^1$ to $R^8$ is independently a hydrogen atom or an alkyl group having 1 to 20 carbon atoms, and at least one of $Y^1$ to $Y^3$ is independently an alkylsulfonyl group having 1 to 20 carbon atoms, arylsulfonyl group having 6 to 20 carbon atoms, alkylcarbonyl group having 2 to 20 carbon atoms or arylcarbonyl group having 7 to 20 carbon atoms, 2l+m is an integer of 6 to 16, and M is Cu, AlCl, TiO or VO. As the number of l and/or m increases, the absorption wave-length can be elongated, whereby an extensive heat ray range can be covered. In addition, as the number of the alkylsulfonyl group and/or the arylsulfonyl group and/or the alkylcarbonyl group and/or the arylcarbonyl group increases, the solubility and the durability of the compound can be improved.

Furthermore, the absorption wavelength can be elongated by coordinating the substituents on the benzene rings of the phthalocyanine with metals. No particular restriction is put on the kind of metal with which the substituents on the benzene rings of the phthalocyanine are coordinated, and any metal can be used, so long as the metal has a coordination ability. Nevertheless, examples of such a metal include copper, zinc, cobalt, nickel, ruthenium, rhodium, palladium, manganese, magnesium, titanium, aluminum, tin and chromium. Of these metals, copper is particularly preferable.

The near infrared ray absorbing compound having the high durability of the present invention can be obtained by, for example, reacting a phthalocyanine represented by the above-mentioned formula (2) with at least one of a 2-aminothiophenol derivative represented by the above-mentioned formula (3) and its analogs, and then carrying out sulfonamidation and/or amidation and/or imidation.

In formula (2), a halogen atom an alkoxy group having 1 to 20 carbon atoms, aryloxy group having 6 to 20 carbon atoms, alkylthio group having 1 to 20 carbon atoms, arylthio group having 6 to 20 carbon atoms, alkylamino group having 1 to 20 carbon atoms and arylamino group having 6 to 20 carbon atoms, which are represented by Z, are the same as in the above-mentioned formula (1). Moreover, in the preferable phthalocyanine represented by the above-mentioned formula (2), each Z is independently a halogen such as fluorine, chlorine, bromine or iodine, and p is an integer of 6 to 16. That is to say, the 2-aminothiophenol represented by formula (3) is easily reacted with the halogen atom on a phthalocyanine ring to obtain the desired compound. M is a divalent metallic atom, or a trivalent or a tetravalent substituted metal or oxymetal, as in the above-mentioned formula (1). From the viewpoints of the stability and the manufacture easiness of the phthalocyanine, M is preferably Cu, AlCl, TiO or VO, and above all, Cu is particularly preferable.

The phthalocyanine in which Z is the chlorine atom or the bromine atom is easily available in the market, and the phthalocyanine in which Z is the iodine atom can be prepared by replacing the chlorine atom or the bromine atom on the phthalocyanine with the iodine atom in accordance with a usual technique, e.g., by using potassium iodide or sodium iodide. In addition, the fluorinated phthalocyanine can be prepared from a fluorinated phthalonitrile by a method described in "Dyes and Pigment", p. 91 (1992).

Examples of the particularly preferable phthalocyanine represented by formula (2) include C.I. Pigment Green 7 (trade name Phthalocyanine Green), C.I. Pigment Green 36, C.I. Pigment Green 37 and C.I. Pigment Green 38, and they are industrially easily available as the halogenated phthalocyanines.

In the 2-aminothiophenol represented by formula (3), an alkyl group having 1 to 20 carbon atoms and an aryl group having 6 to 20 carbon atoms represented by $Y^4$ are the same as in formula (1). An alkyl group having 1 to 20 carbon atoms, aryl group having 6 to 20 carbon atoms, alkoxy group having 1 to 20 carbon atoms and aryloxy group having 6 to 20 carbon atoms represented by $R^9$ to $R^{12}$ are the same as represented by $R^1$ to $R^8$ in the above-mentioned formula (1). In general, these 2-aminothiophenol derivatives can easily be prepared by a method described in "Synthesis", p. 288 (1985). The particularly preferable compound of formula (3) is a compound having a hydrogen atom or alkyl group as substituents $R^9$ to $R^{12}$. Moreover, instead of the direct use of the compound (3), an analog of the compound (3) can be used. That is to say, compounds which can produce the compound (3) during the reaction under the undermentioned basic reaction conditions-are included in the analogs of the present invention. For example, compounds represented by the following formulae can produce the compound (3) during the reaction, and they can provide the same product as in the case that the compound (3) is used at the start time of the process:

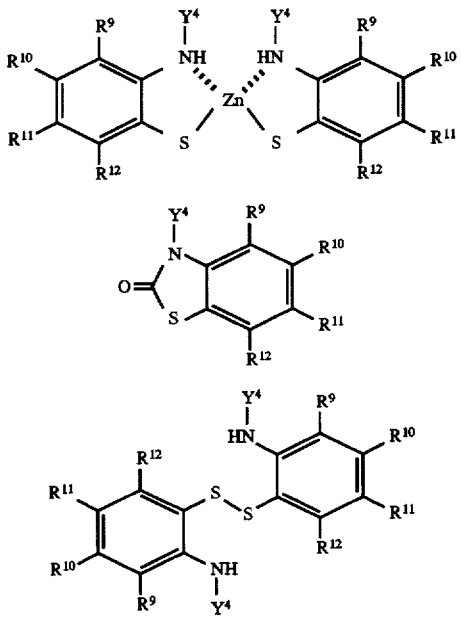

wherein $Y^4$ and $R^9$ to $R^{12}$ are the same as in formula (3).

The reaction of the phthalocyanine represented by formula (2) with the 2-aminothiophenol derivative represented by formula (3) can be carried out under usual conditions for a nucleophilic reaction, i.e., in the presence of a base such as sodium hydroxide, potassium hydroxide, sodium carbonate, potassium carbonate, sodium hydride or t-butoxypotassium. Alternatively, if the compound of formula (3) is used in the form of an isolated sodium salt, potassium salt or zinc salt, the amount of the base can be decreased, or the reaction can be done without using any base.

This reaction may be carried out in the presence of a solvent, and examples of such a solvent include polar solvents such as dimethylformamide (DMF), dimethyl sulfoxide (DMSO), N,N'-dimethylimidazolidinone (DMI) and sulfolane, ketone solvents such as acetone and methyl ethyl ketone, and aromatic hydrocarbon solvents such as toluene, xylene, monochlorobenzene and dichlorobenzene.

In general, the phthalocyanine represented by formula (2) and the base (4 to 100 equivalents per equivalent of the phthalocyanine) are dissolved or suspended in the solvent (1 to 1000 times as much as weight of the phthalocyanine), and the 2-aminothiophenol derivative represented by formula (3) or its analog (4 to 100 equivalents per equivalent of the phthalocyanine) is added thereto with stirring and reaction is then done at 50° to 220° C. The addition of the 2-aminothiophenol derivative or its analog may be made before, during or after the heating. Furthermore, this addition may be done at once, or the 2-aminothiophenol derivative or its analog may be added portionwise. Alternatively, the 2-aminothiophenol derivative itself may be used as the solvent, and after the addition of the base, the phthalocyanine may be added. One kind or some kinds of selected 2-aminothiophenols may be used. Moreover, a nucleophilic reagent such as thiols and alcohols other than 2-aminothiophenols or their analogs can simultaneously be used. The reaction may be carried out under atmospheric pressure or an increased pressure, and as a reaction accelerator, a quaternary ammonium salt, crown ether or the like may be added.

The progress of the reaction can be determined by, for example, measuring the $\lambda_{max}$ of the reaction solution.

After the completion of the reaction, for the accomplishment of the sulfonamidation and/or amidation and/or imidation, there are a first method which comprises adding an amidating agent and/or an imidating agent to the reaction mixture, and then continuing the reaction, and a second method which comprises once isolating an intermediate, i.e., the phthalocyanine reacted with 2-aminothiophenol derivative, and then carrying out the sulfonamidation, amidation and/or imidation.

In the first method, the amidating agent and/or the imidating agent is added to the reaction mixture to carry out the reaction, the amount of the amidating agent and/or the imidating agent being in the range of 1 to 100 equivalents per equivalent of the phthalocyanine. Examples of the amidating agent and the imidating agent include sulfonic acid halides such as methylsulfonic acid chloride, trifluoromethylsulfonic acid chloride, ethylsulfonic acid chloride, benzenesulfonic acid chloride and toluenesulfonic acid chloride, carboxylic anhydrides such as acetic anhydride, propionic anhydride, butyric anhydride, pentanoic anhydride, hexanoic anhydride, heptanoic anhydride, octanoic anhydride and benzoic anhydride, carboxylic dianhydrides such as succinic anhydride, maleic anhydride and phthalic anhydride, carboxylic acid esters such as ethyl acetate, propyl acetate, butyl acetate, ethyl propionate, ethyl butyrate, ethyl pentanoate, ethyl hexanoate, ethyl heptanoate, ethyl octanoate, diethyl succinate, diethyl maleate and diethyl phthalate, and carboxylic acid halides such as acetyl chloride, acetyl bromide, ethylcarbonyl chloride, propylcarbonyl chloride, butylcarbonyl chloride, pentylcarbonyl chloride, hexylcarbonyl chloride, heptylcarbonyl chloride and benzoyl chloride. After the completion of the reaction, the reaction mixture is usually poured into water or an alcohol such as methanol, ethanol, propanol, butanol or pentanol to precipitate the desired compound. The thus precipitated product is separated by filtration, preferably under suction, washed with water, further washed with an alcohol to remove salts, the remaining base, the unreacted 2-aminothiophenol derivative and the unreacted amidating agent or imidating agent, and then dried to isolate the near infrared ray absorbing compound of the present invention.

In the second method, the mixture obtained after the reaction of the compounds having formulae (2) and (3) is usually poured into water or an alcohol such as methanol, ethanol, propanol, butanol or pentanol to precipitate a phthalocyanine compound reacted with aminothiophenol. The thus precipitated compound is separated by filtration, preferably under suction, washed with water, further washed with an alcohol to remove salts, the remaining base and the unreacted 2-aminothiophenol derivative, and then dried to isolate the compound. The successive amidation or imidation is carried out in a pyridine solvent or in a solvent such as toluene, xylene or methylene chloride in the presence of a tertiary amine such as triethylamine by adding the sulfonamidating agent, the amidating agent or the imidating agent in an amount of 1 to 100 equivalents per equivalent of the starting phthalocyanine and by stirring the mixture at a temperature of 0° to 150° C. In this case, a reaction accelerator such as dimethylaminopyridine can be added. After the completion of the reaction, the isolation of the desired product is done in the same manner as in the above-mentioned first method.

The obtained near infrared ray absorbing compound of the present invention can easily be dissolved in an organic solvent such as toluene, xylene or ethyl acetate, and therefore, if necessary, it can be purified by column chromatography.

The near infrared ray absorbing compound of the present invention is a highly soluble type compound which has an absorption in a long wave range and a high heat resistance and which is easily soluble in a resin or a solvent. In its preparation method, an inexpensive pigment can be utilized as a starting material, and the reaction is also simple. The product obtained by the method of the present invention is not a single compound but a mixture of several kinds of compounds, and in consequence, the absorption wavelength of the product is relatively broad. Thus, the obtained product can broadly absorb a near infrared ray range, and for this reason, the product can easily be applied to near infrared ray absorbing materials such as a coating composition, a near infrared ray absorbing filter, and it is also suitable for the absorption of heat rays.

The metal coordinated phthalocyanine can be obtained by reacting the above-mentioned phthalocyanine with a metallic salt. Examples of the metallic salt include fluorides, chlorides, bromides, sulfates, nitrates, acetates, oxalates and acetylacetonates of metals having the above-mentioned coordination ability. The coordination can be formed by stirring the phthalocyanine and the metallic salt in an aprotic polar solvent such as N,N-dimethylformamide, N-methylpyrrolidone or tetrahydrofuran, and in this case, if necessary, a base such as sodium hydroxide, potassium hydroxide, sodium hydride, potassium hydride or potassium carbonate can be added. In compliance with the obtained compound, a solvent such as methanol, ethanol, isopropanol or acetone can also be used. Alternatively, the reaction can be carried out in a two-layer system solvent of water and toluene, xylene, benzene, chloroform or methylene chloride. In this case, if necessary, a base such as sodium hydroxide, potassium hydroxide, potassium carbonate or sodium carbonate, or a surface active agent can be added in an amount of 0.01 to 1000 equivalents per equivalent of the original phthalocyanine.

The amount of the metallic salt is in the range of 1 to 100 equivalents per equivalent of the original phthalocyanine. No particular restriction is put on the amount of the solvent to be used, but it is usually in the range of 1 to 1000 times as much as the weight of the original phthalocyanine.

In the coordination of the metal, a ratio of the metal to nitrogen atoms which are substituents on the benzene rings of the phthalocyanine is 1:1, 1:2, 1:3, 1:4 or the like. In the case of 1:2, 1:3 or 1:4, the metal is coordinated with two or more nitrogen atoms in the molecule, or the coordination is achieved between the molecules. In the case that the metal is coordinated, the absorption wavelength is broader than in the case that the metal is not coordinated, so that an absorption range extends to a range of 900 to 1500 nm.

No particular restriction is put on a method for preparing a heat ray absorbing material from the near infrared ray absorbing compound, but for example, the following three methods can be utilized.

(1) The near infrared ray absorbing compound is kneaded with a resin, and then heated and molded to prepare a resin plate or a resin film.

(2) A coating composition containing the near infrared ray absorbing compound is prepared, and a transparent resin plate, a transparent film or a transparent glass is then coated with this coating composition.

(3) The near infrared ray absorbing compound is added to an adhesive, and this adhesive containing the same is then used to prepare a sandwich resin plate, a sandwich resin film, a sandwich glass or the like.

In the first place, in the method (1) which comprises kneading the near infrared ray absorbing compound with the resin, and then heating and molding the kneaded material, the resin which can give the highest possible transparency to the prepared resin plate or resin film is preferable. Examples of such a resin include polyethylene, vinyl-based resins such as polystyrene, polyacrylic acid, polyacrylic acid esters, polyvinyl acetate, polyacrylonitriles, polyvinyl chloride and polyvinyl fluoride, and addition polymers of these vinyl-based resins, polymethacrylic acid, polymethacrylic acid esters, polyvinylidene chloride, polyvinylidene fluoride, polyvinylidene cyanide, copolymers of vinyl-based resins or fluorine-based resins such as vinylidene fluoride-trifluoroethylene copolymer, vinylidene fluoride-tetrafluoroethylene copolymer and vinylidene cyanide-vinyl acetate copolymer, fluorine-containing resins such as polytrifluoroethylene, polyterafluoroethylene and polyhexafluoropropylene, polyamides such as nylon 6 and nylon 66, polyimides, polyurethane, polypeptides, polyesters such as polyethylene terephthalate, polycarbonates, polyethers such as polyoxymethylenes, polyethylene oxides and polypropylene oxides, epoxy resin, polyvinyl alcohol and polyvinyl butyral, but they are not restrictive.

In the preparation method of the film, a molding temperature, conditions of film formation and the like depend upon the selected resin to some extent, but the film can be obtained by a method which usually comprises adding the near infrared ray absorbing compound to the powder or the pellets of the base resin, heating and melting the mixture at 150° to 350° C., molding or extruding it to obtain a near infrared ray absorbing resin plate having a thickness of 0.1 to 100 mm, or a method which comprises forming a film by an extruder, or forming a raw film by the extruder, and then monoaxially or biaxially stretching it at 30° to 120° C. by twice or 5 times to obtain the film having a thickness of 10 to 200 µm. Alternatively, the near infrared ray absorbing material can also be prepared by cast-polymerizing the near infrared ray absorbing compound of the present invention droxide, and a resin monomer such as an acrylic resin or a prepolymer of the resin monomer in the presence of a polymerization initiator. At the time of the kneading, there may be added additives such as an ultraviolet light absorber and a plasticizer which can usually be used in the molding of the resin. The amount of the near infrared ray absorbing compound to be added depends upon the thickness of the product, a desired absorption power, a desired heat ray transmittance, a desired visible light transmittance and the like, but it is usually in the range of 1 ppm to 10%.

In order to accomplish the preparation of the coating composition and the coating, there are a method which comprises dissolving the near infrared ray absorbing compound of the present invention in a binder resin and an organic solvent to prepare the coating composition, and another method which comprises finely granulating the phthalocyanine compound to several micro meters or less, and then dispersing it in an acrylic emulsion to prepare the aqueous coating composition. In the former method, examples of the usable binder resin include aliphatic ester resins, acrylic resins, melamine resins, urethane resins, aromatic ester resins, polycarbonate reins, aliphatic polyolefin resins, aromatic polyolefin resins, polyvinyl resins, polyvinyl alcohol resins, modified polyvinyl resins (PVB, EVA and the like) and copolymer resins thereof. Examples of the usable solvent include halogen solvents, alcohol solvents, ketone solvents, ester solvents, aliphatic hydrocarbon solvents, aromatic hydrocarbon solvents, ether solvents and mixtures thereof. The concentration of the near infrared ray absorbing compound depends upon the thickness of a coating film, a desired absorption intensity, a desired heat ray transmittance, a desired visible light transmittance and the like, and it is usually in the range of 0.1 to 100% based on the weight of the binder resin. Furthermore, the concentration of the binder resin is usually in the range of 1 to 50% based on the total weight of the coating composition. The aqueous acrylic emulsion coating composition can similarly be obtained by dispersing the fine powder (50 to 500 nm) of the near infrared ray absorbing compound in the uncolored acrylic emulsion coating. Some additives such as an ultraviolet light absorber and an antioxidant which can be used in an ordinary coating composition may be added to the coating composition.

The coating composition prepared by either of the above-mentioned methods can be applied onto a transparent resin film, a transparent resin plate, a transparent glass plate or the like by a bar coater, a blade coater, a spin coater, a reverse coater, a die coater or a spray to form a heat ray absorbing filter. In order to protect the coated surface, a protective layer can be formed thereon, or a transparent resin plate, a transparent resin film or the like can be laminated on the coated surface. In this connection, a cast film is also included in the present invention.

In the method (3) which comprises adding the near infrared ray absorbing compound to the adhesive, and then forming the sandwich resin plate, the sandwich resin film, a sandwich glass or the like, examples of the usable adhesive include known transparent adhesives such as polyvinyl butyral adhesives (PVB) for usual silicone resins, urethane resins, acrylic resins and the like and sandwich glasses, and ethylene-vinyl acetate adhesives (EVA) for the sandwich glasses. The resin plates, the resin plate and the resin film, the resin plate and the glass plate, the resin films, the resin film and the glass plate, or the glass plates can be stuck to each other by the use of the adhesive containing 0.1 to 50% of the near infrared ray absorbing compound to form the heat ray absorbing filter. Alternatively, a technique of thermo-compression bonding can be used.

On one surface or both the surfaces of the heat ray absorbing filter formed in the above-mentioned manner, an ultraviolet light cutting layer, a hard coat layer or an anti-reflective layer can be formed, or an adhesive layer is formed, whereby the filter can become further usable. If necessary, the heat ray absorbing filter can be combined with a heat ray reflecting layer formed by alternately laminating a metal oxide such as indium oxide, tin oxide or zinc oxide and a metal such as gold or silver by sputtering, or a heat ray reflecting coating composition prepared by finely granulating a metal mixture mainly comprising a copper salt or zinc oxide, a tungsten compound, $YbPO_4$, ITO (tin-doped indium oxide), ATO (tin-doped antimony oxide) or the like to an average particle diameter of 100 μm or less.

Next, the present invention will be described in more detail with reference to examples, but the scope of the present invention should not be limited to these examples at all.

EXAMPLE 1

C.I. Pigment Green 7 (Phthalocyanine Green) (10.0 g, 8.87 mmol), 2-(n-octylamino)thiophenol (33.7 g, 142 mmol, 16 equivalents) and potassium carbonate (39.2 g, 284 mmol, 32 equivalents) were reacted at 120° C. for 5 hours in dimethylformamide (200 ml). After being cooled to room temperature, the reaction mixture was poured into methanol (500 ml). Afterward, the resulting precipitate was collected by filtration under suction, washed with methanol, further washed with water, and then dried to isolate a phthalocyanine compound (26.5 g). Next, the phthalocyanine compound was dissolved in a pyridine solvent (300 ml), and acetyl chloride (7.0 g, 89.2 mmol) was added thereto at room temperature for 1 hour and reaction was then carried out at 50° C. for 2 hours. The reaction mixture was poured into ice water (1000 ml). The resulting precipitate was collected by filtration under suction, washed with water, further washed with methanol, and then dried to obtain a near infrared ray absorbing mixture (29.4 g) containing a compound represented by formula (4).

The mixture was easily dissolved in an aromatic solvent such as toluene or benzene (in toluene, 5% or more of the mixture could be dissolved ), and the $\lambda_{max}$ of the mixture was 943 nm (in toluene).

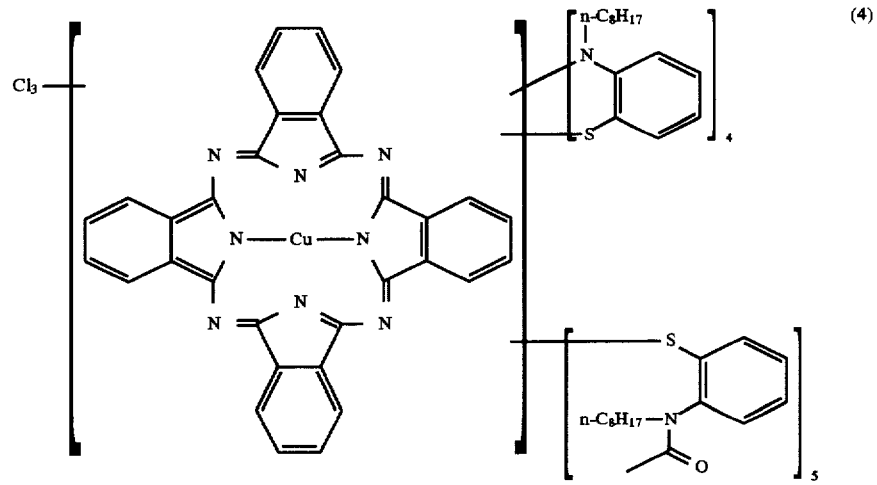

Furthermore, the mixture was mixed with polyethylene terephthalate pellets 1203 made by Unitika Ltd. in a ratio of 0.03:1, melted at 260° to 280° C., and then extruded into a film having a thickness of 100 μm by an extruder. Afterward, this film was biaxially stretched to form a near infrared ray absorbing filter having a thickness of 25 μm. The formed filter could sufficiently absorb a light of 700 to 1100 nm. The $T_V$ (visible light transmittance) and the $T_E$ (sun-light energy transmittance) of the filter were measured in accordance with JIS-R-3106 by the use of a spectrophotometer UV-3100 made by Shimadzu Corp., and as a result, it was apparent that they were 51% and 42%, respectively.

The filter was subjected to a light-resistant test for 1000 hours by the use of a carbon arc lamp (63° C.), but the deterioration of its absorption by the decomposition of the dyestuff was scarcely observed. Accordingly, the filter was excellent in light resistance.

EXAMPLE 2

C.I. Pigment Green 7 (Phthalocyanine Green) (10.0 g, 8.87 mmol), 2-(n-octylamino)thiophenol (19.0 g, 80.0 mmol, 9 equivalents), 2-aminothiophenol (5.55 g, 44.3 mmol, 5 equivalents) and potassium carbonate (39.2 g, 284 mmol, 32 equivalents) were reacted at 120° C. for 10 hours in dimethylformamide (200 ml). After being cooled to room temperature, the reaction mixture was poured into methanol (500 ml). Afterward, the resulting precipitate was collected by filtration under suction, washed with methanol, further washed with water, and then dried to isolate a phthalocyanine compound (25.6 g). Next, the phthalocyanine compound and 4-dimethylaminopyridine (1.0 g, 8.19 mmol) were dissolved in a pyridine solvent (300 ml), and benzoyl chloride (13.0 g, 92.5 mmol) was added (room temperature, 1 hour) and reaction was then carried out at 50° C. for 2 hours. The reaction mixture was poured into ice water (1000 ml). The resulting precipitate was collected by filtration under suction, washed with water, further washed with methanol, and then dried to obtain a near infrared ray absorbing mixture (30.4 g) containing a compound represented by formula (5).

The mixture was easily dissolved in an aromatic solvent such as toluene or benzene (in toluene, 5% or more of the mixture could be dissolved ), and the $\lambda_{max}$ of the mixture was 960 nm (in toluene).

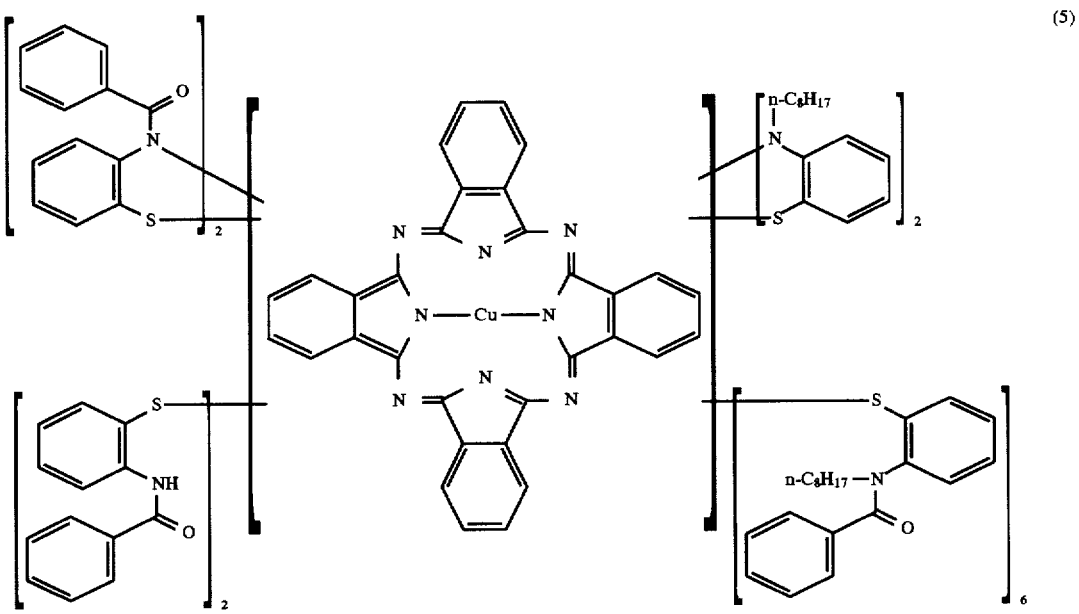

(5)

Furthermore, the mixture was treated in the same manner as in Example 1, thereby forming a near infrared ray absorbing filter having a thickness of 25 μm. This filter could sufficiently absorb a light of 700 to 1100 nm. The filter was subjected to a light-resistant test for 1000 hours by the use of a carbon arc lamp (63° C.), but the deterioration of its absorption by the decomposition of the dyestuff was scarcely observed. Accordingly, the filter was excellent in light resistance.

EXAMPLE 3

C.I. Pigment Green 7 (Phthalocyanine Green) (10.0 g, 8.87 mmol), 2-aminothiophenol (16.7 g, 133 mmol, 15 equivalents) and potassium carbonate (39.2 g, 284 mmol, 32 equivalents) were reacted at 120° C. for 5 hours in dimethylformamide (200 ml). After being cooled to room temperature, the reaction mixture was poured into methanol (500 ml). Afterward, the resulting precipitate was collected by filtration under suction, washed with methanol, further washed with water, and then dried to isolate a phthalocyanine compound (19.5 g). Next, the phthalocyanine compound and 4-dimethylaminopyridine (1.0 g, 8.19 mmol) were dissolved in a pyridine solvent (300 ml), and 2-ethylhexanoyl chloride (25.0 g, 154 mmol) was added thereto at room temperature for 1 hour and reaction was then carried out at 50° C. for 2 hours. The reaction mixture was poured into ice water (1000 ml). The resulting precipitate was collected by filtration under suction, washed with water, further washed with methanol, and then dried to obtain a near infrared ray absorbing mixture (23.4 g) containing a compound represented by formula (6).

The mixture was easily dissolved in an aromatic solvent such as toluene or benzene (in toluene, 5% or more of the mixture could be dissolved ), and the $\lambda_{max}$ of the mixture was 950 nm (in toluene).

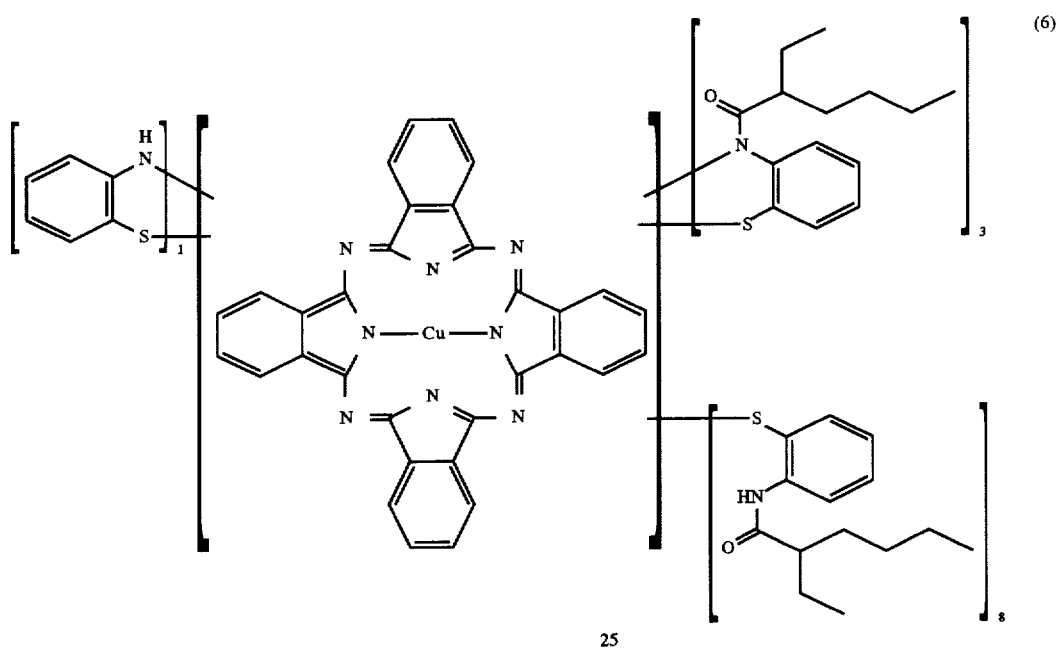

Furthermore, the mixture was treated in the same manner as in Example 1, thereby forming a near infrared ray absorbing filter having a thickness of 25 μm. This filter could sufficiently absorb a light of 700 to 1100 nm. The filter was subjected to a light-resistant test for 1000 hours by the use of a carbon arc lamp (63° C.), but the deterioration of its absorption by the decomposition of the dyestuff was scarcely observed. Accordingly, the filter was excellent in light resistance.

EXAMPLE 4

A phthalocyanine compound (25.6 g) obtained by reacting C.I. Pigment Green 7, 2-(n-octylamino)thiophenol and 2-aminothiophenol in Example 2 was dissolved in a pyridine solvent (300 ml), and phthalic anhydride (3.9 g, 26.3 mmol) was added thereto at room temperature and reaction was then carried out at 100° C. for 1 hour. The reaction mixture was poured into ice water (1000 ml). The resulting precipitate was collected by filtration under suction, washed with water, further washed with methanol, and then dried to obtain a near infrared ray absorbing mixture (26.9 g) containing a compound represented by formula (7).

The mixture was easily dissolved in an aromatic solvent such as toluene or benzene (in toluene, 5% or more of the mixture could be dissolved ), and the $\lambda_{max}$ of the mixture was 960 nm (in toluene).

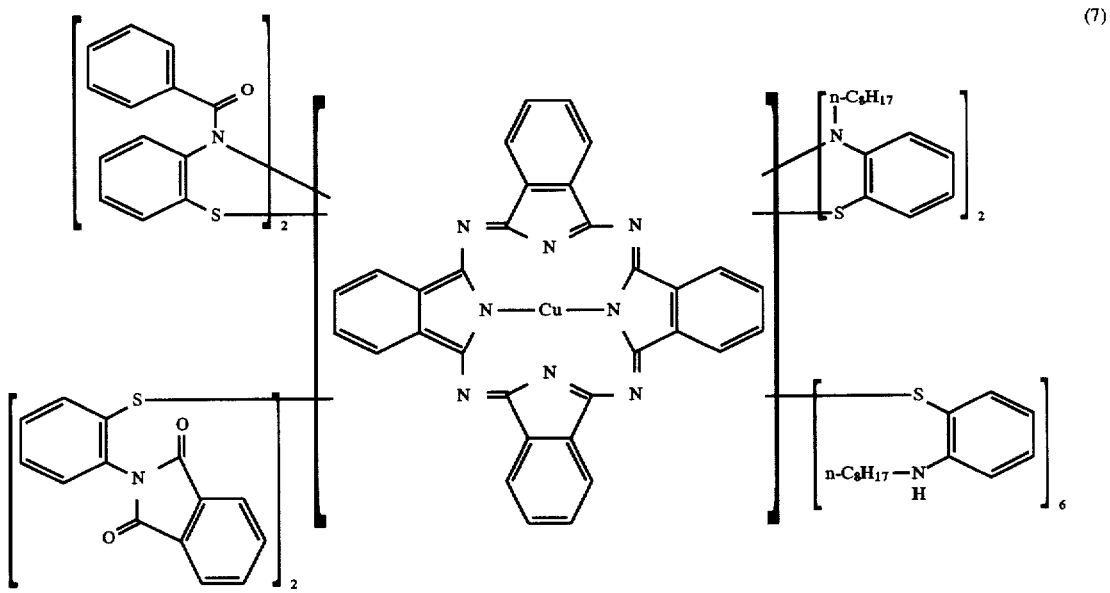

Furthermore, the mixture was treated in the same manner as in Example 1, thereby forming a near infrared ray absorbing filter having a thickness of 25 μm. This filter could sufficiently absorb a light of 700 to 1100 nm. Next, the filter was subjected to a light-resistant test for 1000 hours by the use of a carbon arc lamp (63° C.), but the deterioration of its absorption by the decomposition of the dyestuff was scarcely observed. Accordingly, the filter was excellent in light resistance.

EXAMPLE 5

A phthalocyanine compound (25.6 g) obtained by reacting C.I. Pigment Green 7, 2-(n-octylamino)thiophenol and 2-aminothiophenol in Example 2 was dissolved in a pyridine solvent (300 ml), and acetic anhydride (7.0 g, 68.6 mmol) was added thereto at room temperature and reaction was then carried out at 100° C. for 1 hour. The reaction mixture was poured into ice water (1000 ml). The resulting precipitate was collected by filtration under suction, washed with water, further washed with methanol, and then dried to obtain a near infrared ray absorbing mixture (25.9 g) containing a compound represented by formula (8).

The mixture was easily dissolved in an aromatic solvent such as toluene or benzene (in toluene, 5% or more of the mixture could be dissolved ), and the $\lambda_{max}$ of the mixture was 960 nm (in toluene).

into ice water (1000 ml). The resulting precipitate was collected by filtration under suction, washed with water, further washed with methanol, and then dried to obtain a near infrared ray absorbing mixture (13.9 g).

The mixture was easily dissolved in an aromatic solvent such as toluene or benzene (in toluene, 5% or more of the mixture could be dissolved ), and the $\lambda_{max}$ of the mixture was 920 nm (in toluene).

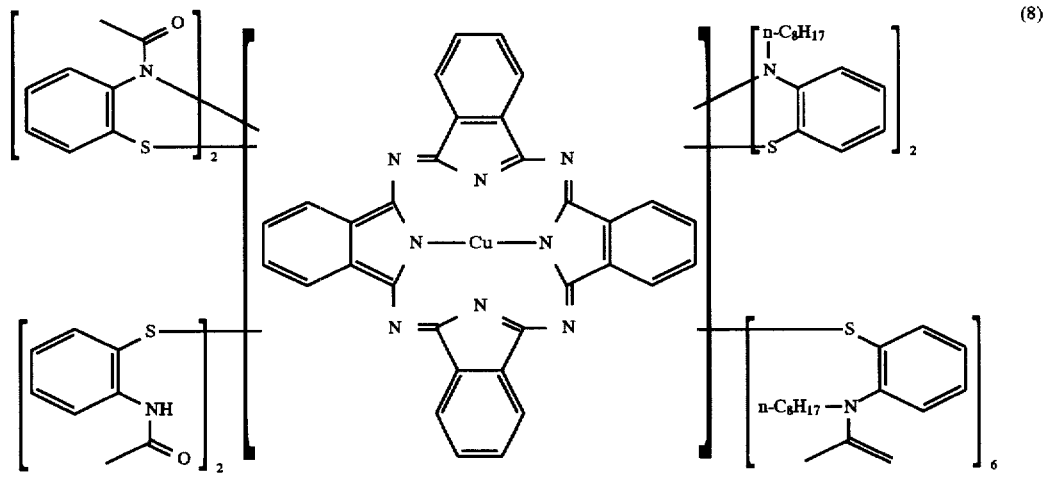

Furthermore, the mixture was treated in the same manner as in Example 1, thereby forming a near infrared ray absorbing filter having a thickness of 25 μm. This filter could sufficiently absorb a light of 700 to 1100 nm. Next, the filter was subjected to a light-resistant test for 1000 hours by the use of a carbon arc lamp (63° C.), but the deterioration of its absorption by the decomposition of the dyestuff was scarcely observed. Accordingly, the filter was excellent in light resistance.

EXAMPLE 6

A phthalocyanine (10.0 g, 6.49 mmol) represented by the following formula (9), 2-aminothiophenol (8.1 g, 64.7 mmol, 10 equivalents) and potassium carbonate (17.9 g, 130 mmol, 20 equivalents) were reacted at 120° C. for 5 hours in dimethylformamide (200 ml). After being cooled to room temperature, the reaction mixture was poured into methanol (500 ml). Afterward, the resulting precipitate was collected by filtration under suction, washed with methanol, further washed with water, and then dried to isolate a phthalocyanine compound (13.5 g). Next, the phthalocyanine compound was dissolved in a pyridine solvent (200 ml), and acetic anhydride (7.0 g, 68.56 mmol) was added thereto at room temperature for 1 hour and reaction was then carried out at 50° C. for 2 hours. The reaction mixture was poured

EXAMPLE 7

A phthalocyanine (7.7 g, 8.88 mmol) represented by the following formula (10), 2-aminothiophenol (16.7 g, 133 mmol, 15 equivalents) and potassium carbonate (39.2 g, 284 mmol, 32 equivalents) were reacted at 120° C. for 5 hours in dimethylformamide (200 ml). After being cooled to room temperature, the reaction mixture was poured into methanol (500 ml). Afterward, the resulting precipitate was collected by filtration under suction, washed with methanol, further washed with water, and then dried to isolate a phthalocyanine compound (15.6 g). Next, the phthalocyanine compound and 4-dimethylaminopyridine (1.0 g, 8.19 mmol) were dissolved in a pyridine solvent (300 ml), and 2-ethylhexanoyl chloride (25.0 g, 154 mmol) was added (room temperature, 1 hour) and reaction was then carried out at 50° C. for 2 hours. The reaction mixture was poured into ice water (1000 ml). The resulting precipitate was collected by filtration under suction, washed with water, further washed with methanol, and then dried to obtain a near infrared ray absorbing mixture (16.4 g) containing a compound represented by formula (11).

The mixture was easily dissolved in an aromatic solvent such as toluene or benzene (in toluene, 5% or more of the mixture could be dissolved ), and the $\lambda_{max}$ of the mixture was 1010 nm (in toluene).

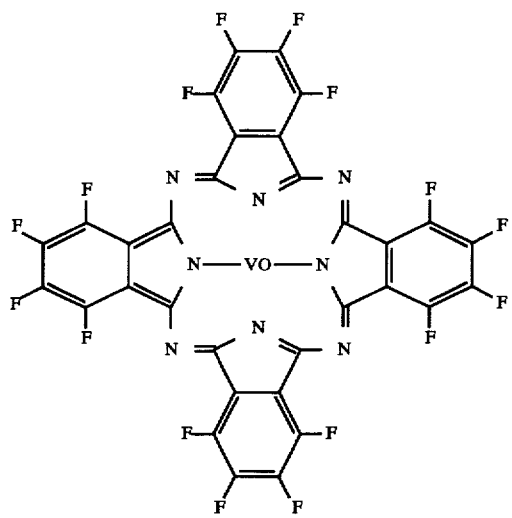

(10)

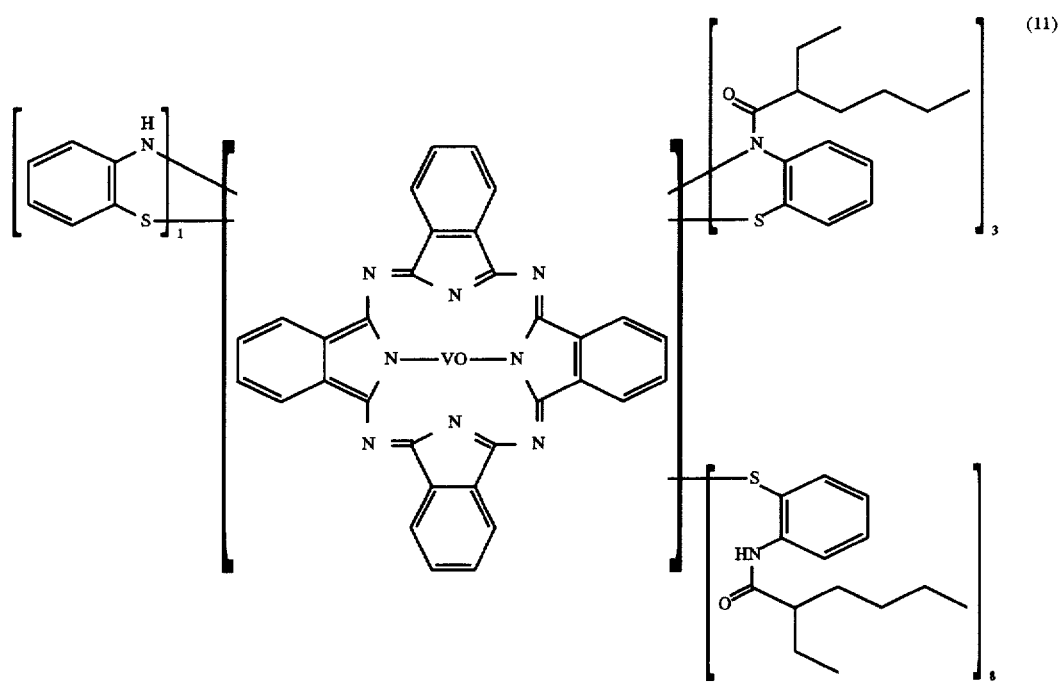

(11)

EXAMPLE 8

Reaction was carried out by all the same procedure as in Example 2 except that benzoyl chloride was replaced with p-trifluoromethylbenzoyl chloride (19.3 g, 92.5 mmol), thereby obtaining a near infrared ray absorbing mixture (29.8 g) containing a compound represented by formula (12).

The mixture was easily dissolved in an aromatic solvent such as toluene or benzene (in toluene, 5% or more of the mixture could be dissolved), and the $\lambda_{max}$ of the mixture was 955 nm (in toluene).

(12)

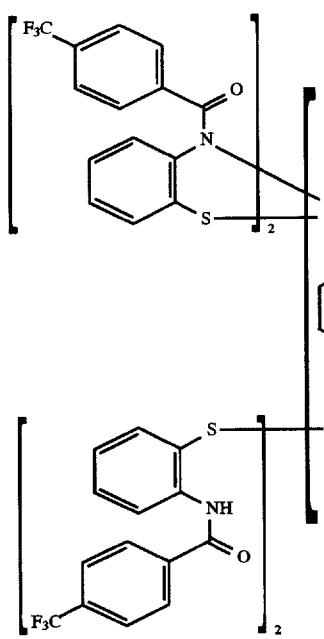 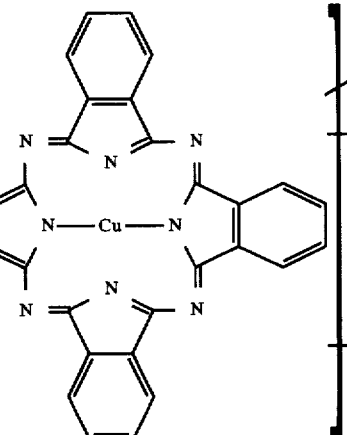 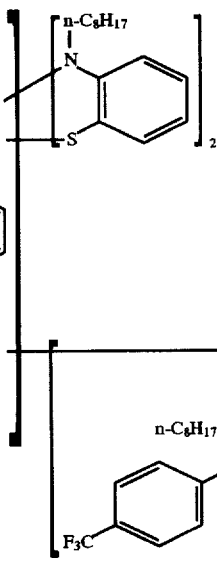

EXAMPLE 9

C.I. Pigment Green 7 (Phthalocyanine Green) (10.0 g, 8.87 mmol), aminoethanethiol (6.8 g, 88.7 mmol, 10 equivalents), 2-aminothiophenol (5.55 g, 44.3 mmol, 5 equivalents) and potassium carbonate (39.2 g, 284 mmol, 32 equivalents) were reacted at 120° C. for 10 hours in dimethylformamide (200 ml). After being cooled to room temperature, the reaction mixture was poured into methanol (500 ml). Afterward, the resulting precipitate was collected by filtration under suction, washed with methanol, further washed with water, and then dried to isolate a phthalocyanine compound (20.6 g). Next, the phthalocyanine compound and 4-dimethylaminopyridine (1.0 g, 8.19 mmol) were dissolved in a pyridine solvent (300 ml), and benzoyl chloride (13.0 g, 92.5 mmol) was added (room temperature, 1 hour) and reaction was then carried out at 50° C. for 2 hours. The reaction mixture was poured into ice water (1000 ml). The resulting precipitate was collected by filtration under suction, washed with water, further washed with methanol, and then dried to obtain a near infrared ray absorbing mixture (25.4 g) containing a compound represented by the following formula (13).

The mixture was easily dissolved in an aromatic solvent such as toluene or benzene (in toluene, 5% or more of the mixture could be dissolved ), and the $\lambda_{max}$ of the mixture was 915 nm (in toluene).

(13)

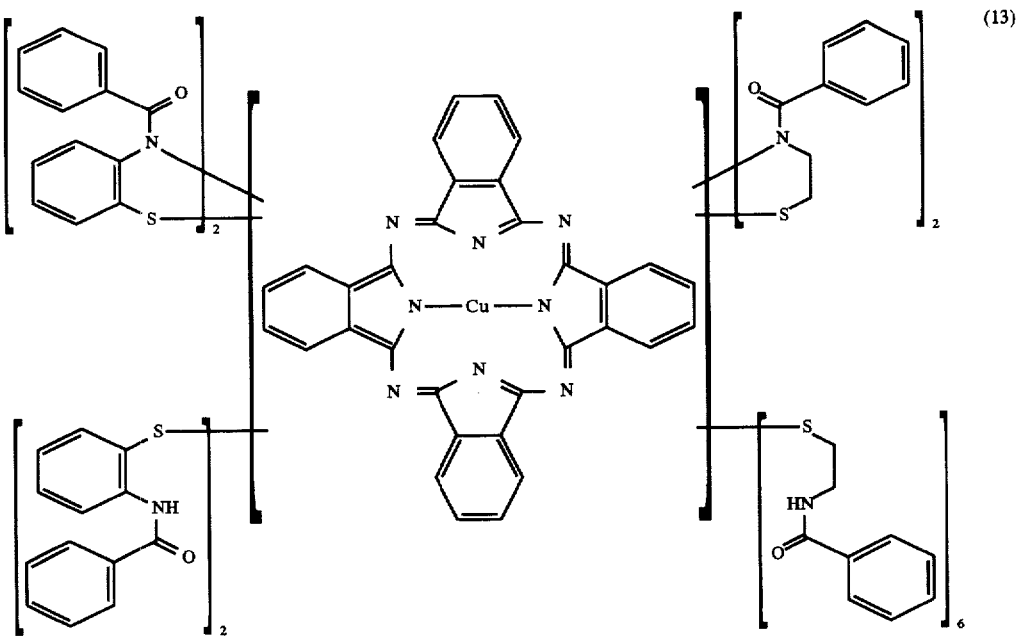

Furthermore, 2.0 g of the mixture, 100 g of Tinuvine 329 (made by Ciba-Geigy, a benzotriazole-based ultraviolet light absorber), 100 g of Seesorb™ 501 (made by Sipro Chemical Co., Ltd., an ultraviolet light absorber) and 10 kg of a polycarbonate (Panlite™ K-1300Z, made by Teijin Limited) were molten and kneaded at 260° to 280° C., and then extruded into a near infrared ray absorbing filter having a thickness of 2 mm by an extruder. Afterward, an acrylic film containing an ultraviolet light absorber and having a thickness of 50 μm was thermally laminated on the above-mentioned near infrared ray absorbing filter. The acrylic film had been formed by mixing 100 g of Tinuvin P™ (made by Ciba-Geigy) of a benzotriazole-based ultraviolet light absorber, 100 g of Uvinal™ 3039 (made by BASF Co., Ltd.) of a cyanoacetic acid-based ultraviolet light absorber and 10 kg of polymethyl methacrylate (PMMA) (Delpe™ 80N, made by Asahi Chemical Industry Co., Ltd.), melting and extruding the mixture at 260° to 280° C. into a raw film having a thickness of 200 μm by the use of an extruder, and then biaxially stretching this raw film.

This filter could sufficiently absorb a light of 700 to 1100 nm, and the $T_V$ and the $T_E$ of the filter were 48% and 39%, respectively.

The filter was subjected to a light-resistant test for 1000 hours by the use of a carbon arc lamp (63° C.), but the deterioration of its absorption by the decomposition of the dyestuff was scarcely observed. Accordingly, the filter was excellent in light resistance.

EXAMPLE 10

Reaction was carried out by all the same procedure as in Example 2 except that 2-(n-octylamino)thiophenol was replaced with 80.0 mmol of 2-(benzylamino)thiophenol, thereby obtaining a near infrared ray absorbing mixture (28.4 g) containing a compound represented by formula (14). This mixture was easily dissolved in an aromatic solvent such as toluene or benzene (in toluene, 5% or more of the mixture could be dissolved ), and the $\lambda_{max}$ of the mixture was 960 nm (in toluene).

Furthermore, 10 g of the above-mentioned mixture was mixed with 10 kg of polymethyl methacrylate (PMMA) (DelpetTm 80N, made by Asahi Chemical Industry Co., Ltd.), and the mixture was melted at 260° to 280° C., and then extruded into a near infrared ray absorbing filter having a thickness of 3 mm by an extruder. This filter could sufficiently absorb a light of 700 to 1100 nm. Next, the filter was subjected to a light-resistant test for 1000 hours by the use of a carbon arc lamp (63° C.), but the deterioration of its absorption by the decomposition of the dyestuff was scarcely observed. Accordingly, the filter was excellent in light resistance.

EXAMPLE 11

Reaction was carried out by all the same procedure as in Example 10 except that 2-(benzylamino)thiophenol was replaced with 40.0 mmol of its derivative (formula 15), thereby obtaining a near infrared ray absorbing mixture containing a compound represented by formula (14) as in Example 10.

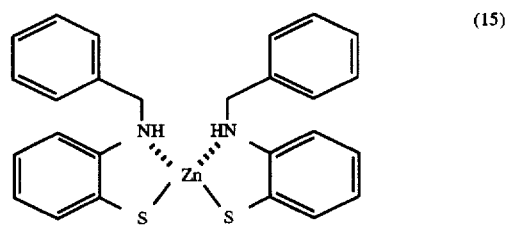

EXAMPLE 12

Reaction was carried out by the same procedure as in Example 10 except that 2-(benzylamino)thiophenol was replaced with 80.0 mmol of its derivative (formula 16), thereby obtaining a near infrared ray absorbing mixture containing a compound represented by formula (14) as in Example 10.

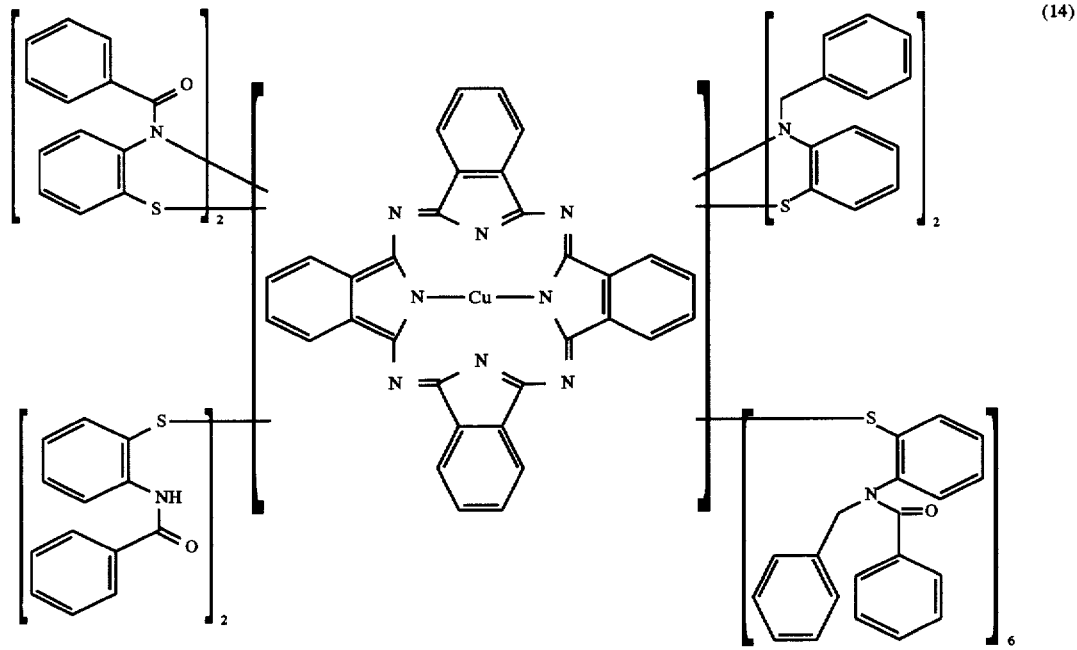

(16)

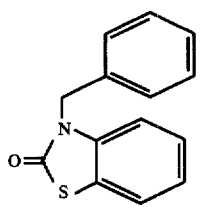

EXAMPLE 13

Reaction was carried out by the same procedure as in Example 10 except that 2-(benzylamino)thiophenol was replaced with 40.0 mmol of its derivative (formula 17), thereby obtaining a near infrared ray absorbing mixture containing a compound represented by formula (14) as in Example 10.

(17)

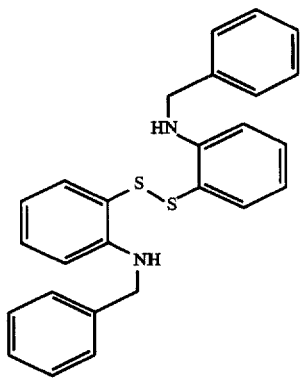

EXAMPLE 14

5 g of a near infrared ray absorbing mixture containing a compound of formula (14) prepared in Example 10, 0.1 g of a red dyestuff for toning (made by Mitsui Toatsu Chemicals, Inc., HSo-147) and 10 g of an ultraviolet light absorber Tinuvin™ 327 (made by Ciba-Geigy) were dissolved in 300 ml of ethyl cellosolve, and 200 g of an acrylic coating composition Almatex™ L1043 (made by Mitsui Toatsu Chemicals, Inc.) was then added thereto, thereby preparing a near infrared ray absorbing coating composition. When a glass plate or a plastic plate was coated with this coating composition, an excellent heat ray absorbing power could be imparted.

EXAMPLE 15

A near infrared ray absorbing mixture (2.5 g) obtained in Example 2 was dissolved in a tetrahydrofuran solvent (25 ml), and copper chloride (II) dihydrate (1.25 g) was added thereto. Next, the solution was stirred at room temperature for 1 hour to accomplish the coordination of copper. This mixture was filtered, and the filtrate was then poured into hexane (100 ml). The resulting precipitate was collected by filtration under suction, washed with hexane, and then dried to obtain a near infrared ray absorbing mixture (2.52 g) containing a compound represented by the following formula (18). Here, the numbers of coordinating Cu and Cl are average values.

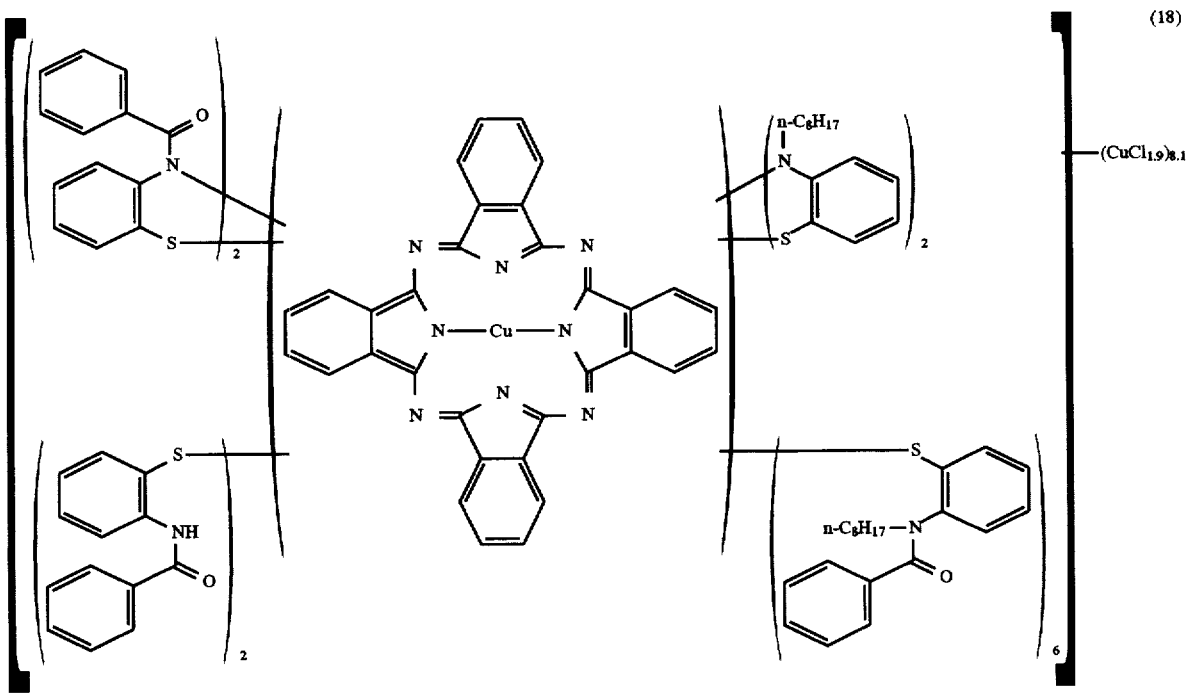

This mixture was dissolved in an aromatic solvent such as toluene or benzene, and the $\lambda_{max}$ of the mixture was 1300 nm (in chloroform). The absorption spectrum of the mixture is shown in FIG. 1. As can be understood from FIG. 1, the absorption wavelength was broadened and so an absorption range was extended, from which the coordination of the metal was confirmed.

Elemental analysis:

C: 57.38, H: 4.72, N: 5.28

S: 7.19, Cu: 9.8, Cl: 10.3

Furthermore, the mixture was mixed with polyethylene terephthalate pellets 1203 made by Unitika Ltd. in a ratio of 0.02:1, melted at 260° to 280° C., and then extruded into a film having a thickness of 100 µm by an extruder. Afterward, this film was biaxially stretched to form a near infrared ray absorbing filter having a thickness of 25 µm. The formed filter could sufficiently absorb a light of 800 to 1500 nm. The $T_V$ and the $T_E$ of the filter were measured in the same manner as in Example 1, and as a result, they were 48% and 46%, respectively.

EXAMPLE 16

Figure 2:
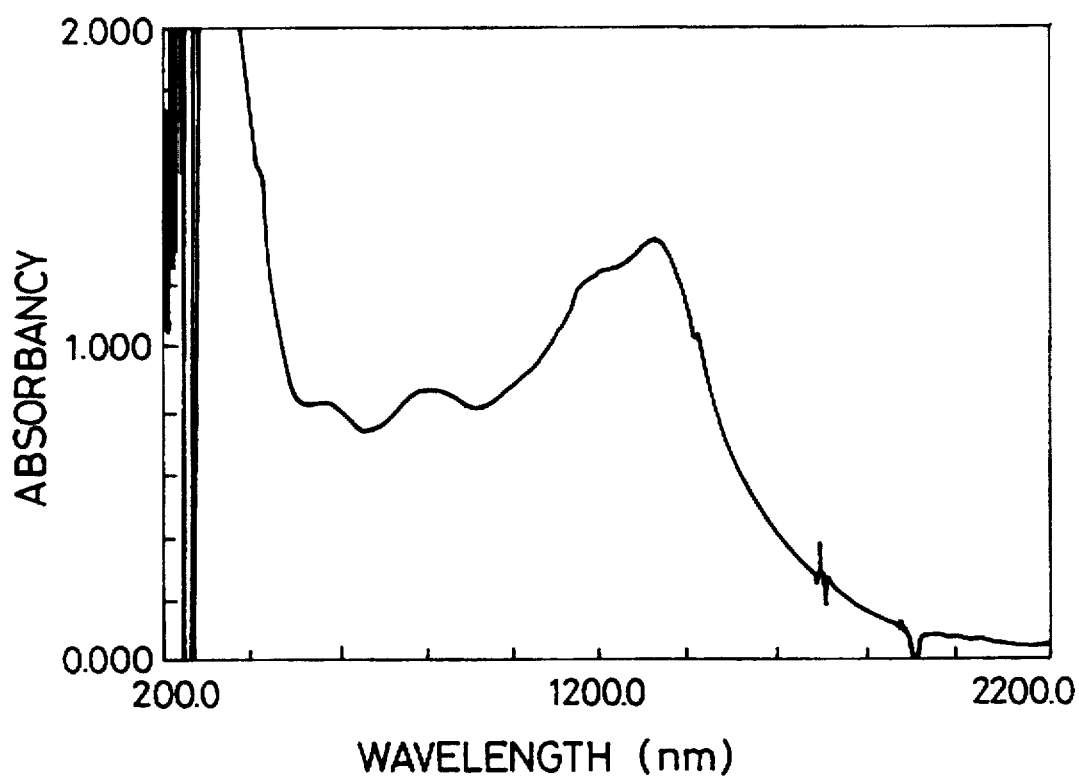
FIG. 2 is a graph showing the absorbency spectrum of a compound obtained in Example 16.

A near infrared ray absorbing mixture (2.5 g) obtained in Example 5 was dissolved in a tetrahydrofuran solvent (25 ml), and copper bromide (II) (2.0 g) was added thereto. Next, the mixture was stirred at room temperature for 1 hour to accomplish the coordination of copper. This mixture was filtered, and the filtrate was then poured into hexane (100 ml). The resulting precipitate was collected by filtration under suction, washed with methanol, and then dried to obtain a near infrared ray absorbing mixture (2.9 g) containing a compound represented by the following formula (19). Here, the numbers of coordinating Cu and Br are average values.

can be understood from FIG. 2, the absorption wavelength was broadened and so the absorption range was extended, from which the coordination of the metal was confirmed.

Elemental analysis:

C: 49.92, H: 4.61, N: 5.71

S: 7.91, Cu: 9.5, Br: 21.3

Furthermore, the mixture was treated in the same manner as in Example 15 to form a near infrared ray absorbing filter having a thickness of 25 µm. This filter could sufficiently absorb a light of 800 to 1500 nm. The $T_V$ and the $T_E$ of the filter were measured in the same manner as in Example 1, and as a result, they were 45% and 44%, respectively.

EXAMPLE 17

A near infrared ray absorbing mixture (2.5 g) obtained in Example 3 was dissolved in a tetrahydrofuran solvent (25 ml), and copper bromide (II) (2.0 g) was added thereto. Next, the solution was stirred at room temperature for 1 hour to accomplish the coordination of copper. This mixture was filtered, and the filtrate was then poured into hexane (100 ml). The resulting precipitate was collected by filtration under suction, washed with hexane, and then dried to obtain a near infrared ray absorbing mixture (2.78 g) containing a compound represented by the following formula (20). Here, the numbers of coordinating Cu and Br are average values.

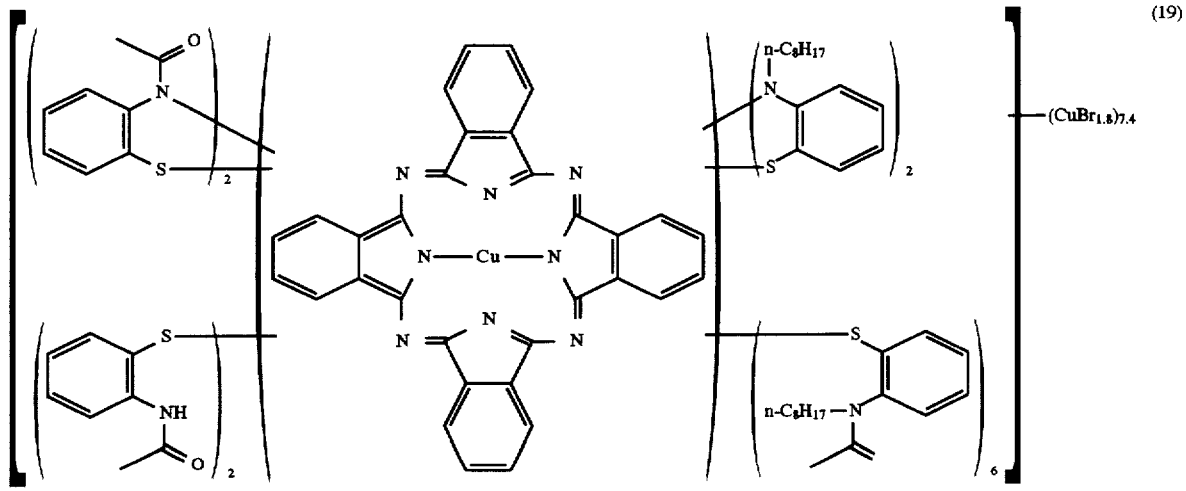

This mixture was dissolved in an aromatic solvent such as toluene or benzene, chloroform, acetone or the like, and the $\lambda_{max}$ of the mixture was 1300 nm (in chloroform). The absorption spectrum of the mixture is shown in FIG. 2. As

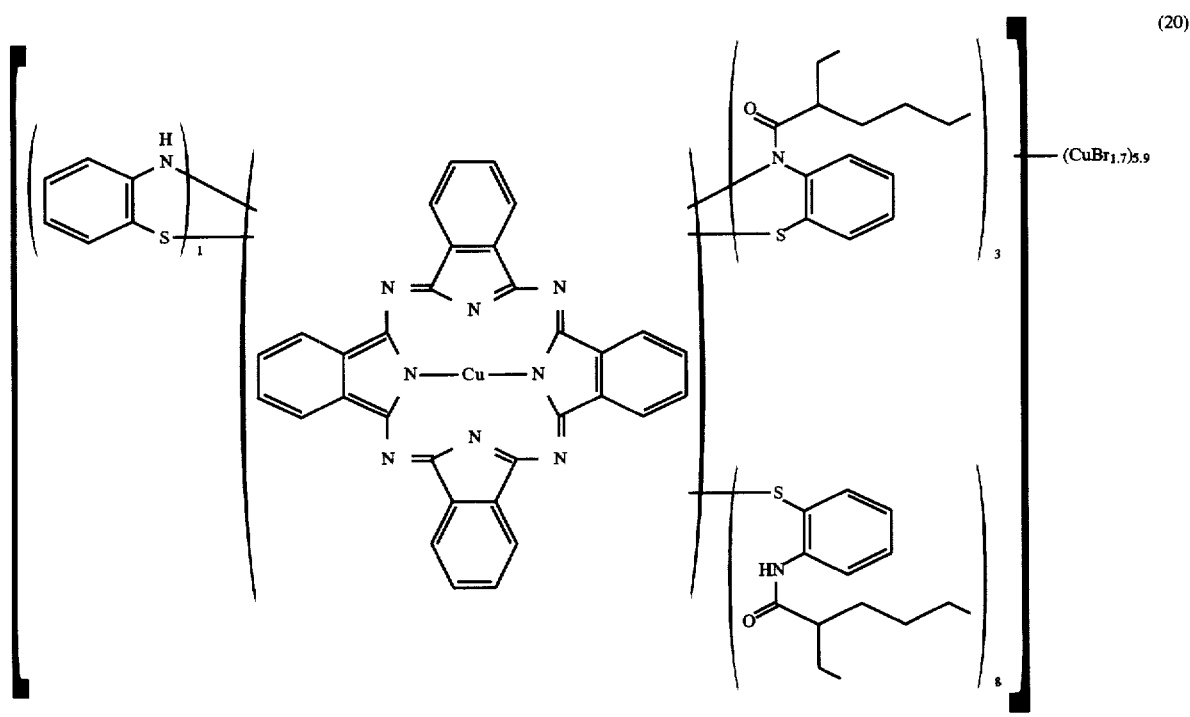

This mixture was dissolved in an aromatic solvent such as toluene or benzene, chloroform, acetone or the like, and the $\lambda_{max}$ of the mixture was 1310 nm (in chloroform).

Furthermore, the mixture was treated in the same manner as in Example 3 to form a near infrared ray absorbing filter having a thickness of 25 μm. This filter could sufficiently absorb a light of 800 to 1500 nm. The $T_V$ and the $T_E$ of the filter were measured in the same manner as in Example 1, and as a result, they were 52% and 53%, respectively.

What is claimed is:

1. A near infrared ray absorbing compound having a high durability represented by formula (1):

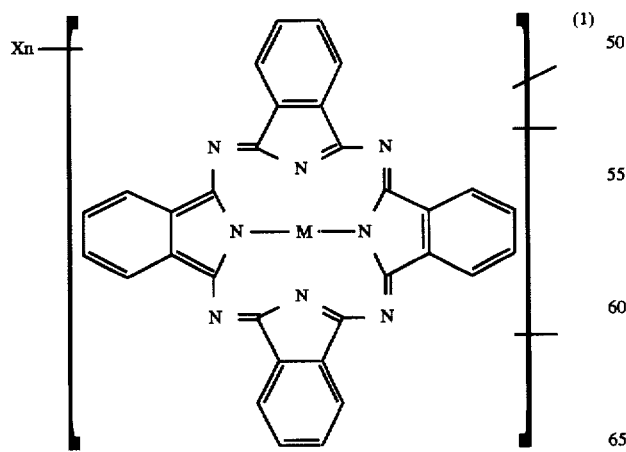

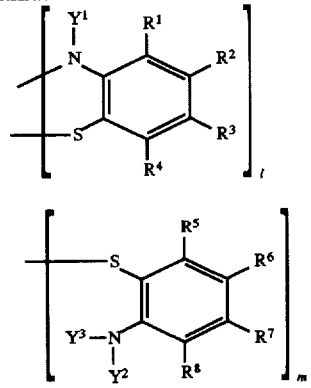

-continued wherein each X is independently a hydrogen atom, halogen atom, hydroxyl group, alkoxy group having 1 to 20 carbon atoms, aryloxy group having 6 to 20 carbon atoms, alkylthio group having 1 to 20 carbon atoms, arylthio group having 6 to 20 carbon atoms, alkylamino group having 1 to 20 carbon atoms, arylamino group having 6 to 20 carbon atoms or alkylarylamino group having 7 to 20 carbon atoms, and the two adjacent Xs may form a five-membered ring or a six-membered ring via two heteroatoms; each of $R^1$ to $R^8$ is independently a hydrogen atom, alkyl group having 1 to 20 carbon atoms, aryl group having 6 to 20 carbon atoms, alkoxy group having 1 to 20 carbon atoms or aryloxy group having 6 to 20 carbon atoms; each of $Y^1$ to $Y^3$ is independently a hydrogen atom, alkyl group having 1 to 20 carbon atoms, aryl group having 6 to 20 carbon atoms, alkylsulfonyl group having 1 to 20 carbon atoms, arylsulfonyl group having 6 to 20 carbon atoms, alkylcarbonyl group having 2 to 20 carbon atoms or arylcarbonyl group having 7 to 20 carbon atoms, and $Y^2$ to $Y^3$ on one nitrogen atom may form a cyclic imide, with the proviso that the compound has at least one of $Y^1$ to $Y^3$ which is an alkylsufonyl group having 1 to 20 carbon atoms, arylsulfonyl group having 6 to 20 carbon atoms, alkylcarbonyl group having 2 to 20 carbon atoms or arylcarbonyl group having 7 to 20 carbon atoms, or which has at least one pair of $Y^2$ to $Y^3$ on one independent nitrogen atom that forms a cyclic imide; n is an integer of 0 to 14; l is an integer of 1 to 8; m is an integer of 0 to 14, subject to n+2l+m=16; and M is a divalent metallic atom, or a trivalent or a tetravalent substituted metal or oxymetal.

2. The near infrared ray absorbing compound having a high durability according to claim 1 wherein, in formula (1), each of the Xs is independently a hydrogen atom or a halogen atom, and each of $R^1$ to $R^8$ is independently a hydrogen atom or an alkyl group having 1 to 20 carbon atoms, and at least three of all of $Y^1$ to $Y^3$ are independently an alkylsulfonyl group having 1 to 20 carbon atoms, arylsulfonyl group having 6 to 20 carbon atoms, alkylcarbonyl group having 2 to 20 carbon atoms or arylcarbonyl group having 7 to 20 carbon atoms, 2l+m is in the range of 6 to 16, and M is Cu, AlCl, TiO or VO.

3. A near infrared ray absorbing compound in which substituents on the benzene rings of the phthalocyanine obtained by reacting a near infrared ray absorbing compound having a high durability described in claim 1 with a metallic salt are coordinated with metals.

4. The near infrared ray absorbing compound according to claim 3 wherein the metallic salt is a copper compound.

5. A near infrared ray absorbing resin composition which contains a near infrared ray absorbing compound described in claim 1.

6. A heat ray absorbing material which contains a near infrared ray absorbing compound described in claim 1.

7. A near infrared ray absorbing resin composition which contains a near infrared ray absorbing compound described in claim 3.

8. A heat ray absorbing material which contains a near infrared ray absorbing compound described in claim 3.

9. A process for preparing a near infrared ray absorbing compound having a high durability described in claim 1 which comprises the steps of reacting a phthalocyanine represented by formula (2):

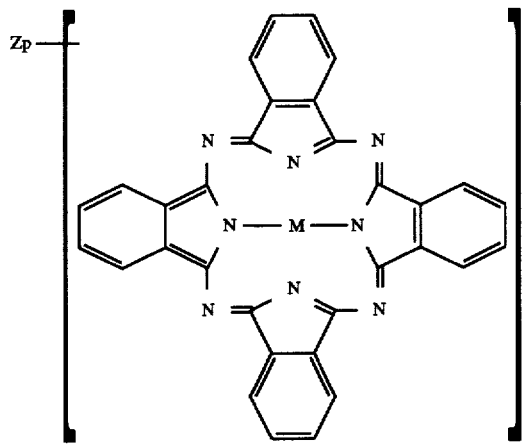
(2)

wherein each Z is independently a halogen atom, alkoxy group having 1 to 20 carbon atoms, aryloxy group having 6 to 20 carbon atoms, alkylthio group having 1 to 20 carbon atoms, arylthio group having 6 to 20 carbon atoms, alkylamino group having 1 to 20 carbon atoms or arylamino group having 6 to 20 carbon atoms, and at least 4 of Zs are the halogen atoms; p is an integer of 4 to 16; and M is a divalent metallic atom, or a trivalent or a tetravalent substituted metal or oxymetal, with at least one of a 2-aminothiophenol derivative represented by formula (3):

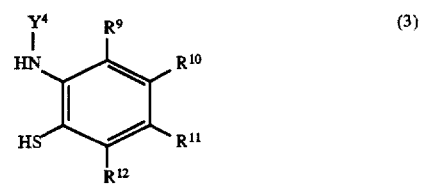
(3)

wherein $Y^4$ is a hydrogen atom, alkyl group having 1 to 20 carbon atoms or aryl group having 6 to 20 carbon atoms; and each of $R^9$ to $R^{12}$ is a hydrogen atom, alkyl group having 1 to 20 carbon atoms, aryl group having 6 to 20 carbon atoms, alkoxy group having 1 to 20 carbon atoms or aryloxy group having 6 to 20 carbon atoms, and its analogs, and then carrying out sulfoamidation and/or amidation and/or imidation.

10. The process for preparing a near infrared ray absorbing a compound having a high durability according to claim 9 wherein an agent for sulfoamidation, amidation or imidation is selected from the group consisting of a sulfonic acid halide, a carboxylic acid halide, a carboxylic anhyride, maleic anhydride, succinic anhydride and phthalic anhydride.

11. The process for preparing a near infrared ray absorbing compound having a high durability according to claim 10 wherein, in formula (2), Z is a halogen atom, p is an integer of 6 to 16, and M is Cu, AlCl, TiO or VO, and in formula (3), each of $R^9$ to $R^{12}$ is a hydrogen atom or an alkyl group.

12. The process for preparing a near infrared ray absorbing compound having a high durability according to claim 9 wherein the phthalocyanine represented by formula (2) is C.I. Pigment Green 7, C.I. Pigment Green 36, C.I. Pigment Green 37 or C.I. Pigment Green 38.

* * * * *

UNITED STATES PATENT AND TRADEMARK OFFICE
CERTIFICATE OF CORRECTION

PATENT NO. : 5,788,914
DATED : August 4, 1998
INVENTOR(S) : Oi, et al

It is certified that error appears in the above-identified patent and that said Letters Patent is hereby corrected as shown below:

On the title page, insert the following after item [22],

-- [30] Foreign Application Priority Data
October 2, 1995 [JP] Japan....................................................7-254925
October 13, 1995 [JP] Japan....................................................7-265245 ---

Signed and Sealed this

Second Day of March, 1999

Attest:

Attesting Officer

Q. TODD DICKINSON

Acting Commissioner of Patents and Trademarks